(12) United States Patent
Chait et al.

(10) Patent No.: US 11,971,408 B2
(45) Date of Patent: *Apr. 30, 2024

(54) METHODS AND DEVICES FOR ANALYZING SPECIES TO DETERMINE DISEASES

(71) Applicant: Cleveland Diagnostics, Inc., Cleveland, OH (US)

(72) Inventors: Arnon Chait, Bay Village, OH (US); Boris Y. Zaslavsky, Solon, OH (US)

(73) Assignee: Cleveland Diagnostics, Inc., Cleveland, OH (US)

( * ) Notice: Subject to any disclaimer, the term of this patent is extended or adjusted under 35 U.S.C. 154(b) by 74 days.

This patent is subject to a terminal disclaimer.

(21) Appl. No.: 16/804,313

(22) Filed: Feb. 28, 2020

(65) Prior Publication Data

US 2020/0209243 A1    Jul. 2, 2020

Related U.S. Application Data

(63) Continuation of application No. 14/420,166, filed as application No. PCT/US2013/054059 on Aug. 8, 2013, now Pat. No. 10,613,087.

(60) Provisional application No. 61/681,814, filed on Aug. 10, 2012.

(51) Int. Cl.
  *G01N 33/574*    (2006.01)
  *G16H 50/20*    (2018.01)
  *G16H 50/30*    (2018.01)

(52) U.S. Cl.
  CPC ..... *G01N 33/574* (2013.01); *G01N 33/57407* (2013.01); *G01N 33/57488* (2013.01); *G01N 33/57492* (2013.01); *G01N 33/57496* (2013.01); *G16H 50/20* (2018.01); *G16H 50/30* (2018.01)

(58) Field of Classification Search
  CPC . G01N 33/574; G01N 33/57407; G16H 50/30
  See application file for complete search history.

(56) References Cited

U.S. PATENT DOCUMENTS

| | | | |
|---|---|---|---|
| 5,008,204 A | 4/1991 | Stehling | |
| 5,241,072 A | 8/1993 | Colon et al. | |
| 5,340,474 A | 8/1994 | Kauvar | |
| 5,734,024 A | 3/1998 | Zaslavsky | |
| 5,769,074 A | 6/1998 | Barnhill et al. | |
| 5,818,231 A | 10/1998 | Smith | |
| 5,948,750 A | 9/1999 | Garsky et al. | |
| 6,136,960 A | 10/2000 | Chait et al. | |
| 6,642,009 B2 | 11/2003 | Hung | |
| 7,011,955 B1 | 3/2006 | Stemmler et al. | |
| 7,100,095 B2 | 8/2006 | Godse et al. | |
| 7,247,498 B2 | 7/2007 | Godec et al. | |
| 7,968,350 B2 * | 6/2011 | Chait | G01N 33/5375 436/536 |
| 8,099,242 B2 | 7/2012 | Chait et al. | |
| 8,211,714 B2 | 7/2012 | Chait et al. | |
| 9,354,229 B2 | 5/2016 | Chait et al. | |
| 9,678,076 B2 | 6/2017 | Chait et al. | |
| 2001/0016590 A1 | 8/2001 | Ahotupa et al. | |
| 2001/0044431 A1 | 11/2001 | Gustavo | |
| 2002/0045198 A1 | 4/2002 | Mikolajczyk | |
| 2003/0083316 A1 * | 5/2003 | Giles | A61K 31/704 514/86 |
| 2003/0016224 A1 | 8/2003 | Chait et al. | |
| 2004/0018519 A1 * | 1/2004 | Wright, Jr. | G01N 33/6848 435/6.14 |
| 2004/0229375 A1 | 11/2004 | Chait et al. | |
| 2004/0236603 A1 | 11/2004 | Heller et al. | |
| 2005/0277137 A1 * | 12/2005 | Lokshin | B82Y 5/00 702/19 |
| 2006/0240416 A1 | 10/2006 | Banerjee et al. | |

(Continued)

FOREIGN PATENT DOCUMENTS

| | | |
|---|---|---|
| WO | WO 99/010522 A1 | 3/1999 |
| WO | WO 00/010674 A1 | 3/2000 |

(Continued)

OTHER PUBLICATIONS

Batterman (The Science of the Total Environment 2002 284:237-247), (Year: 2002).*
Fustinoni (Int Arch Occup Environ Health 2000 73:389-396) (Year: 2000).*
Schmitt (Toxicology 2008 22:457-467) (Year: 2008).*
International Search Report dated Dec. 18, 2003 from International Application No. PCT/US2002/036519, filed Nov. 12, 2002.
Written Opinion dated Apr. 30, 2003 for Application No. PCT/US2002/036519.
International Search Report/Written Opinion, dated Nov. 23, 2004, for PCT/US2004/019343, dated Nov. 23, 2004.

(Continued)

*Primary Examiner* — Changhwa J Cheu
(74) *Attorney, Agent, or Firm* — Wolf, Greenfield & Sacks, P.C.

(57) ABSTRACT

The present invention, in some embodiments thereof, generally relates to methods and devices for determining the health status of a subject, e.g., whether the subject has a disease or other condition. In some embodiments, a plurality or mixture of species may be differentially solubilized in a single two-phase aqueous system, or other multi-phase aqueous system. The nature or degree of the solubilization of the species may be used to determine the health status of a subject. For example, some embodiments are directed to devices and methods for determining a disease or other condition as a function of the changes to the structure of two or more species. The species may be selected based on their differential solubility behavior in a two-phase or other multi-phase aqueous system. Preferential enrichment of the species concentrations in one of the phases, and/or the ratios of species in the phases may be determined, and in some cases compared to their respective values for healthy and/or diseased subjects to determine the health status of the subject.

23 Claims, 4 Drawing Sheets

(56) References Cited

U.S. PATENT DOCUMENTS

| | | | |
|---|---|---|---|
| 2006/0255257 | A1 | 11/2006 | Belgovskiy et al. |
| 2006/0269964 | A1 | 11/2006 | Chait et al. |
| 2007/0042405 | A1* | 2/2007 | Lokshin ............ G01N 33/57449 702/19 |
| 2007/0128618 | A1 | 6/2007 | Chait et al. |
| 2007/0198194 | A1* | 8/2007 | Chait ................ G01N 33/6848 702/19 |
| 2008/0050831 | A1* | 2/2008 | Chait ............... G01N 33/57434 436/63 |
| 2010/0093558 | A1* | 4/2010 | Pandha .............. G01N 33/6872 435/7.1 |
| 2011/0166028 | A1* | 7/2011 | Bergstrom ........... C12Q 1/6886 506/7 |
| 2011/0183328 | A1* | 7/2011 | Taylor .............. G01N 33/57438 435/6.12 |
| 2012/0088692 | A1 | 4/2012 | Chait et al. |
| 2014/0065642 | A1 | 3/2014 | Chait et al. |
| 2015/0219655 | A1 | 8/2015 | Chait et al. |
| 2016/0238607 | A1 | 8/2016 | Chait et al. |
| 2019/0178891 | A1 | 6/2019 | Chait et al. |

FOREIGN PATENT DOCUMENTS

| | | |
|---|---|---|
| WO | WO 01/055698 A1 | 8/2001 |
| WO | WO 03/016883 A1 | 2/2003 |
| WO | WO 03/042694 A2 | 5/2003 |
| WO | WO 2004/111655 A1 | 12/2004 |
| WO | WO 2005/008247 A2 | 1/2005 |
| WO | WO 2005/008247 A3 | 1/2005 |
| WO | WO 2006/124100 A2 | 11/2006 |
| WO | WO 2007/027561 A2 | 3/2007 |
| WO | WO 2008/005043 A2 | 1/2008 |
| WO | WO 2015/200302 A2 | 12/2015 |

OTHER PUBLICATIONS

International Preliminary Examination Report dated Oct. 15, 2003 from International Application No. PCT/US2002/026019.
International Search Report for PCT/US2002/026019 dated Oct. 3, 2002.
Written Opinion dated Apr. 30, 2003 from International Application No. PCT/US2002/026019.
International Search Report and Written Opinion for PCT/US2006/048344 dated Apr. 24, 2008.
International Search Report and Written Opinion for Application No. PCT/US2013/054059 dated Dec. 10, 2013.
International Preliminary Report on Patentability for Application No. PCT/US2013/054059 dated Feb. 19, 2015.
[No Author Listed] Program listing of the Society of Biomolecular Screening 2002, Session 2A Technical Program for the 8th Annual SBS Conference & Exhibition, Sep. 22-26, 2002, Netherlands Congress Centre, The Hague, The Netherlands.
[No Author Listed] Program listing of the Well-Characterized Biologics Conference 2002, California Separation Science Society, WCBP 2002, 6th Symposium on the Interface of Regulatory and Analytical Sciences for Biotechnology Health Products, Jan. 27-30, 2002.
[No Author Listed] QSAR Introduction (web pages; last updated Jul. 2, 2007).
Albertsson et al., Separation processes in biotechnology. Aqueous two-phase separations. Bioprocess Technol. 1990;9:287-327.
Andrews et al., Affinity gel electrophoresis as a predicative technique in the fractionation of transgenic sheep milk proteins by affinity aqueous two-phase partitioning. Biotechnol Lett. 2000;22:1349-1353.
Arnoldi et al., Lipophilicity-Antifungal Activity Relationships for Some Isoflavonoid Phytoalexins. J Agric Food Chem. 1990; 38:834-838.
Atkinson et al., Trypsin and α-Chymotrypsin Partitioning in Polyethylene Glycol/Maltodextrin Aqueous-Two-Phase Systems. Food Bioprod. Proc. Jun. 1994;72:106-112.
Baker et al., In biomarkers we trust? Nat Biotechnol. Mar. 2005;23(3):297-304.
Bast et al., Translational crossroads for biomarkers. Clin Cancer Res. Sep. 1, 2005;11(17):6103-8.
Berggren et al., Substitutions of surface amino acid residues of cutinase probed by aqueous two-phase partitioning. BBA. 2000;1481:317-327.
Bevan et al., A High-Throughput Screening Method for the Determination of Aqueous Drug Solubility Using Laser Nephelometry in Microtiter Plates. Anal. Chem. 2000;72:1781-1787.
Bodnar et al. Exploiting the Complementary Nature of LC/MALDI/MS/MS and LC/ESI/MS/MS for Increased Proteome Coverage. American Society for Mass Spectrometry. 2003;14:971-979.
Chait, From Structure To Signature. 8th Annual SBS Conference & Exhibition, Sep. 22-26, 2002, Netherlands Congress Centre, The Hague, The Netherlands.
Chait, HTS Technology for Analysis of Structural Signatures of Biomolecules: Methodology and Applications. California Separation Science Society, WCBP 2002, 6th Symposium on the Interface of Regulatory and Analytical Sciences for Biotechnology Health Products, Jan. 27-30, 2002.
Durand et al., Protein Glycosylation and Diseases: Blood and Urinary Oligosaccharides as Markers for Diagnosis and Therapeutic Monitoring. Clinical Chemistry. 2000;46(6):795-805.
Everberg et al., Protein pre-fractionation in detergent-polymer aqueous two-phase systems for facilitated proteomic studies of membrane proteins. J Chromatogr A. 2004; 1029:113-124.
Fedotoff et al., Influence of Serum Proteins on Conformation of Prostate-Specific Antigen. J. Biomol Struct. Dynamics. Apr. 1, 2012. 29(5): 1051-1064. DOI:10.1080/073911012010525030.
Guiliano, Aqueous Two-Phase Protein Partitioning Using Textile Dyes as Affinity Ligands. Anal. Biochem. 1991;197:333-339.
Gulyaeva et al., Relative hydrophobicity of organic compounds measured by partitioning in aqueous two-phase systems. Journal of Chromatograph B.2000;743:187-194.
Guzzetta, Reverse Phase HPLC Basics for LC/MS. An IonSource Tutorial, published Jul. 22, 2001.
Harboe et al., Generation of Antibodies to the Signal Peptide of the MPT83 Lipoprotein of Mycobacterium tuberculosis. Scan. J. Immunol. 2002;55:82-87.
Hunger et al., The t(1;19)(q23;p13) results in consistent fusion of E2A and PBX1 coding sequences in acute lymphoblastic leukemias. Blood. 1991;77:687-693.
Kohwi et al., Amphipathic Lipid-Bound Protein Antigens in Mouse Bladder Carcinomas Detected by a Monoclonal Antibody. Biochemistry. 1984;23:5945-5950.
Kuboi, et al., Evaluation of Surface Hydrophobicities of Proteins Using Hydrophobic Interaction with Non-ionic Surfactants in Aqueous Two-Phase Partitioning Systems. Kagaku Kogaku Ronbunshu. 1993;19:446-453.
Labaer et al., So, you want to look for biomarkers (introduction to the special biomarkers issue). J Proteome Res. Jul.-Aug. 2005;4(4):1053-9.
Matsumura et al. A new concept for macromolecular therapeutics in cancer chemotherapy: mechanism of tumoritropic accumulation of proteins and the antitumor Smancs. Cancer Research. 1986;46:6387-92.
Müller et al., Real and Pseudo Oxygen Gradients in Ca-Alginate Beads Monitored During Polarographic $Po_2$-Measurements Using Pt-Needle Microelectrodes. Biotechnology and Bioengineering. 1994;44:617-625.
Peracaula et al., Altered glycosylation pattern allows the distinction between prostate-specific antigen (PSA) from normal and tumor origins. Glycobiology. Jun. 2003;13(6):457-470.
Platt et al., QSAR in grossly underdetermined systems: Opportunities and issues. IBM Journal of Research and Development. 2001;45 (web page).
Richon, A. et al., "An Introduction to QSAR Methodology," (web page; Oct. 1997) Accessed online at http://www.netsci.org/science/compchem/feature19.html.
Sakurai et al., Ligand- and Nuclear Factor-Dependent Change in Hydrophobicity of Thyroid Hormone $ß_1$ Receptor. *Thyroid*. 1998;8(4):343-352.

(56) References Cited

OTHER PUBLICATIONS

Schena et al., Parallel human genome analysis: Microarray-based expression monitoring of 1000 genes. PNAS. Oct. 1996;93:10614-10619.
Singh et al., Gene expression correlates of clinical prostate cancer behavior. Cancer Cell, 2002;1:203-209.
Sniegoski, An Examination Of The Concentration Of Organic Components Water-Extracted From Petroleum Products. Water Research. 1975;9:421-423.
Stovsky et al., Prostate-specific Antigen/Solvent Interaction Analysis: A Preliminary Evaluation of a New Assay Concept for Detecting Prostate Cancer Using Urinary Samples. Urology. Sep. 2011. 78(3):601-605. Epub Jul. 23, 2011. doi: 10.1016/j.urology.2011.03.071.
Stovsky et al., PSA/SIA: A New Highly Sensitive and Specific Structure-Based Assay for Prostate Cancer (poster), AUA NC 82nd Annual Meeting, Chicago, IL, Sep. 24-27, 2008.
Takano et al. Measuring the Solubility of Liquid Organic Compounds in Water. Journal of the Chemical Society of Japan. 1985, (11):2116-2119.
Takano et al., Solubility Measurement of Liquid Organic Compounds in Water. CAS Online. 1985. 105:60254.
Yan, Detection by ozone-induced chemiluminescence in chromatography. Journal of Chromatography. 1999;842:267-308.
Zaslavsky et al., A New Method for Analysis of Components in a Mixture without Preseparation: Evaluation of the Concentration Ratio and Protein-Protein Interaction. Analytical Biochemistry. 2001;296:262-269.
Zaslavsky, Aqueous Two-Phase Partitioning (Book) Marcel Dekker, New York, Ch. 1-10 (1995).
Zaslavsky, Characteristics of Protein-Aqueous Medium Interactions Measured by Partition in Aqueous Ficoll-Dextran Biphasic System. J. Chromatogr. 1983;260:329-336.
International Search Report and Written Opinion mailed Mar. 7, 2023, for Application No. PCT/US2022/046537.
Zaslavsky et al., Analytical applications of partitioning in aqueous two-phase systems: Exploring protein structural changes and protein-partner interactions in vitro and in vivo by solvent interaction analysis method. Biochim Biophys Acta. May 2016;1864(5):622-44. doi: 10.1016/j.bbapap.2016.02.017. Epub Feb. 23, 2016.
Zhong et al., Identification of prohibitin 1 as a potential prognostic biomarker in human pancreatic carcinoma using modified aqueous two-phase partition system combined with 2D-MALDI-TOF-TOF-MS/MS. Tumour Biol. Feb. 2015;36(2):1221-31. doi: 10.1007/s13277-014-2742-y. Epub Oct. 25, 2014.
Da Silva et al., Effect of sodium chloride on solute-solvent interactions in aqueous polyethylene glycol-sodium sulfate two-phase systems. J Chromatogr A. Dec. 18, 2015;1425:51-61. doi: 10.1016/j.chroma.2015.11.019. Epub Nov. 10, 2015.
Da Silva et al.. Analysis of partitioning of organic compounds and proteins in aqueous polyethylene glycol-sodium sulfate aqueous two-phase systems in terms of solute-solvent interactions. J Chromatogr A. Oct. 9, 2015;1415:1-10. doi: 10.1016/j.chroma.2015.08.053. Epub Aug. 28, 2015.
Ferreira et al., Effect of NaCl additive on properties of aqueous PEG-sodium sulfate two-phase system. J Chromatogr A. Jan. 13, 2012;1220:14-20.
Madeira et al., Solvatochromic relationship: Prediction of distribution of ionic solutes in aqueous two-phase systems. J Chromatogr A. 2013; 1271: 10-6.
Madeira et al., Salt effects on solvent features of coexisting phases in aqueous polymer/polymer two-phase systems. J Chromatogr A. Mar. 16, 2012;1229:38-47. doi: 10.1016/j.chroma.2012.01.029. Epub Jan. 18, 2012.
Madeira et al., Solvent properties governing solute partitioning in polymer/polymer aqueous two-phase systems: nonionic compounds. J Phys Chem B. Jan. 14, 2010;114(1):457-62.
U.S. Appl. No. 16/273,253, filed Feb. 12, 2019, Chait et al.
PCT/US2002/036519, Dec. 18, 2003, International Search Report.
PCT/US2002/036519, Apr. 30, 2003, Written Opinion.
PCT/US2004/019343, Nov. 23, 2004, International Search Report and Written Opinion.
PCT/US2002/026019, Oct. 3, 2002, International Search Report.
PCT/US2002/026019, Apr. 30, 2003, Written Opinion.
PCT/US2002/026019, Oct. 15, 2003, International Preliminary Examination Report.
PCT/US2006/048344, Apr. 24, 2008, International Search Report and Written Opinion.
PCT/US2013/054059, Dec. 10, 2013, International Search Report and Written Opinion.
PCT/US2013/054059, Feb. 19, 2015, International Preliminary Report on Patentability.

* cited by examiner collecting a biological fluid from a patient  partitioning the biological fluid in at least one aqueous two-phase partitioning system  assaying the aqueous phase of one phase of the aqueous two phase partitioning system for a plurality of analytes, using at least one assay specific for the each analyte  determining the concentration for each analyte in the aqueous phase, and, calculating presence or risk level of the disease in the patient by comparing the concentrations of the analytes to known concentration values in corresponding aqueous phases derived from biological fluid samples taken from individuals with and without the disease

FIG. 2

METHODS AND DEVICES FOR ANALYZING SPECIES TO DETERMINE DISEASES

RELATED APPLICATIONS

This application is a continuation of U.S. patent application Ser. No. 14/420,166, filed Feb. 6, 2015, entitled "Methods and Devices for Analyzing Species to Determine Diseases," by Chait, et al., which is a national stage filing under 35 U.S.C. § 371 of International Application No. PCT/US2013/054059, filed Aug. 8, 2013, entitled "Methods and Devices for Analyzing Species to Determine Diseases," by Chait, et al., which claims the benefit of U.S. Provisional Patent Application Ser. No. 61/681,814, filed Aug. 10, 2012, entitled "Methods and Devices for Analyzing Species to Determine Diseases," by Chait, et al., each of which is incorporated herein by reference in its entirety.

FIELD

The present invention, in some embodiments thereof, generally relates to methods and devices for determining a disease or condition in a subject. In some embodiments, a plurality of species may be differentially solubilized in a multi-phase aqueous system wherein the nature of solubilization of the species may serve to identify a disease or condition in a subject. In certain cases, the present invention generally relates to methods for diagnosing cancers or other diseases in a subject.

BACKGROUND

Most disease involves a variety of changes in the human body. For example, cancers, viral and bacterial illnesses, genetic conditions, and other ailments generally involve a variety of changes in metabolic systems and biomolecule behavior. As is known in the detection of sepsis, looking at a single biomarker is often not accurate in detecting the condition; analyzing several discreet biomarkers on the other hand may give stronger clues to the possibility of septic shock in a subject.

While monitoring multiple biomarkers may be appealing for accurate disease diagnostics, tracking two or more biomarkers can be a technical challenge, and furthermore, monitoring of the level, expression, or concentration of the biomarkers may be confounded by other conditions leading to the same or different observations. Biomarker proteins may also contain information related to a disease process in their three-dimensional structure and/or interaction with other ligands. The ideal diagnostic system for cancer and other serious illness would therefore allow for a single technical protocol to be applied to a biological sample, wherein structural information related to two or more biomarkers could be worked up in parallel and quickly analyzed for differences related to the underlying disease or condition.

SUMMARY

The subject matter of the present invention involves, in some cases, interrelated products, alternative solutions to a particular problem, and/or a plurality of different uses of one or more systems and/or articles.

It is therefore a purpose, in some embodiments, to describe methods and devices for determining a disease or condition as a function of dissolution pattern of a plurality of species in aqueous phases of a multi-phase partitioning system. In some embodiments of the invention, a single aqueous phase may be analyzed for multi-species presence and biomolecule concentration, without recourse to analyzing concentration of the species in the aqueous portion of the second phase.

The invention includes, in one aspect, a method for diagnosing a predetermined cancer comprised of the following: collecting a biological fluid from a subject; partitioning the biological fluid in an aqueous two-phase partitioning system; assaying aqueous phases of the two phase partitioning system for a plurality of predetermined analytes, using at least one assay specific for the each analyte; calculating a partition coefficient K for each analyte, wherein K is a ratio of amount of dissolved analyte in each aqueous phase of the two phase partitioning system; and, determining presence or risk level of the predetermined cancer in the subject by comparing numerical values of calculated partition coefficients with reference values previously determined for the plurality of analytes in the biological fluid taken from individuals with and without the predetermined cancer.

In one set of embodiments, the assaying is performed with a plurality of analyte specific immuno-based assays.

In another set of embodiments, the analyte specific immuno-based assays include ELISA tests.

In another set of embodiments, the two-phase partitioning system is adapted to differentially partition the plurality of analytes when the predetermined cancer is present or absent in the subject.

In another set of embodiments, the plurality of analytes includes at least two unique biomolecules.

In another set of embodiments, the method is applied as a part of a mathematical or statistical algorithm, optionally in conjunction with information obtained from imaging, genetic, or a biochemical test.

In another set of embodiments, individuals without the predetermined cancer include individuals with benign tumors.

In another set of embodiments, the diagnosing is used to screen, diagnose, classify according to phenotype/genotype, aid in therapeutic course of action, monitor progression, or detect recurrence of the predetermined cancer.

In another set of embodiments, the numerical values of the partition coefficients are used to select a therapeutic drug or course of therapeutic intervention.

In another set of embodiments, the partitioning involves vortexing and centrifugation of the two-phase partitioning system with the plurality of analytes present.

In another set of embodiments, the predetermined cancer is selected from the list: throat cancer, stomach cancer, pancreatic cancer, brain cancer, lung cancer, cervical cancer, prostate cancer, breast cancer, testicular cancer, ovarian cancer, oral cancer, throat cancer, esophagus cancer, and intestinal cancer and intestinal cancer.

In another set of embodiments, the plurality of predetermined analytes is used as biomarkers for the predetermined cancer presence or risk.

In another set of embodiments, the reference values are determined from blood samples taken from individuals with and free of the predetermined cancer.

Another aspect of the invention includes a liquid partitioning system for use in the detection of a predetermined disease in a subject, including: two liquid phases, the liquid phases being substantially immiscible, wherein each liquid phase has an aqueous component wherein a plurality of predetermined analytes associated with the predetermined disease are solubilized, and wherein the concentrations of the predetermined analytes in the liquid phases are related to the presence or absence of the predetermined disease in the subject.

In one set of embodiments, the liquid phases include at least one polymer and at least one salt.

In another set of embodiments, the liquid phases include at least one of polyethylene glycol, dextran, polyvinyleperrolidone, Ficoll®, and copolymer of ethylene glycol and propylene glycol.

In another set of embodiments, the liquid phases are manipulated within a microfluidics element.

In another set of embodiments, the plurality of analytes includes at least two unique biomolecules In another set of embodiments, the plurality of analytes is derived from a human biological fluid.

In another set of embodiments, the biological fluid is selected from the following: whole blood, blood serum, blood plasma, saliva, urine, CNS fluid, breast nipple aspirate fluid, cerebral spinal fluid, and semen.

In another set of embodiments, the system is a component of a disease detection unit.

In another set of embodiments, the predetermined disease is a cancer.

In another set of embodiments, concentrations of the predetermined analytes in at least one of the phases are compared to concentration values for the predetermined analytes in the corresponding phases associated with individuals without and with the predetermined disease.

In another set of embodiments, partition coefficients for the predetermined analytes in the phases are calculated and compared to partition coefficient values for the predetermined analytes associated with individuals without and with the predetermined disease.

Yet another aspect of the invention is generally directed to a method for diagnosing a disease in a subject comprised of the following: collecting an biological fluid from a subject; partitioning the biological fluid in at least one aqueous two-phase partitioning system; assaying the aqueous phase of one phase of the aqueous two phase partitioning system for a plurality of analytes, using at least one assay specific for the each analyte; determining the concentration for each analyte in the aqueous phase, and, calculating presence or risk level of the disease in the subject by comparing the concentrations of the analytes to known concentration values in corresponding aqueous phases derived from biological fluid samples taken from individuals with and without the disease.

In one set of embodiments, the disease is cancer.

In another set of embodiments, the cancer is selected from the following: throat cancer, stomach cancer, pancreatic cancer, brain cancer, lung cancer, cervical cancer, prostate cancer, breast cancer, testicular cancer, ovarian cancer, oral cancer, throat cancer, esophagus cancer, and intestinal cancer and intestinal cancer.

In another set of embodiments, the disease is realized as a plurality of diseases.

In another set of embodiments, the disease is hereditary.

In another set of embodiments, the one phase is substantially immiscible in a second phase of the aqueous two phase partitioning system.

In another set of embodiments, the concentrations in either of the aqueous phases differ between healthy individuals and those affected by the disease.

In another set of embodiments, the biological fluid is selected from the following: whole blood, blood serum, blood plasma, saliva, urine, CNS fluid, breast nipple aspirate fluid, cerebral spinal fluid, and semen.

In yet another aspect, the present invention is generally directed to a method for diagnosing a cancer. In one set of embodiments, the method includes acts of partitioning a biological fluid from a subject in an aqueous two-phase partitioning system, assaying aqueous phases of said two phase partitioning system for a plurality of species, using at least one assay specific for said each species, calculating a partition coefficient K for each species, and determining presence or risk level of said cancer in said subject by comparing the calculated partition coefficients with reference values. K may be a ratio of amount of dissolved species in each aqueous phase of said two phase partitioning system.

According to another aspect, the present invention is generally directed to a method for diagnosing a disease in a subject. In one set of embodiments, the method includes acts of partitioning a biological fluid from a subject in at least one aqueous two-phase partitioning system, assaying at least one phase of said aqueous two phase partitioning system for a plurality of species, using at least one assay specific for said each species, determining the concentration for each species in said aqueous phase, and determining presence or risk level of said disease in said subject by comparing the concentrations of said species to reference values.

Yet another aspect of the present invention is generally directed to a method for determining cancer in a subject. In one set of embodiments, the method includes acts of providing a sample taken from a subject, where the sample comprises two or more species, determining partition coefficients between the two or more species in at least a first phase and a second phase of an aqueous multi-phase system, and determining cancer within the subject based on the two or more partition coefficients. In some cases, the second phase is substantially immiscible with the first phase at equilibrium.

In still another aspect, the present invention is generally directed to a liquid partitioning system for use in the detection of a disease in a subject. In one set of embodiments, the system comprises two or more liquid phases, said liquid phases being substantially immiscible, where each liquid phase has an aqueous component where a plurality of species associated with said disease are solubilized, and where the concentrations of said species in said liquid phases are related to the presence or absence of said disease in said subject.

In another aspect, the present invention encompasses methods of making one or more of the embodiments described herein, for example, as is discussed herein. In still another aspect, the present invention encompasses methods of using one or more of the embodiments described herein, for example, as is discussed herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2 shows a flowchart of method associated with another embodiment of the invention;

DETAILED DESCRIPTION

The present invention, in some embodiments thereof, generally relates to methods and devices for determining the health status of a subject, e.g., whether the subject has a disease or other condition. In some embodiments, a plurality or mixture of species may be differentially solubilized in a single two-phase aqueous system, or other multi-phase aqueous system. The nature or degree of the solubilization of the species may be used to determine the health status of a subject. For example, some embodiments are directed to devices and methods for determining a disease or other condition as a function of the changes to the structure of two or more species. The species may be selected based on their differential solubility behavior in a two-phase or other multi-phase aqueous system. Preferential enrichment of the species concentrations in one of the phases, and/or the ratios of species in the phases may be determined, and in some cases compared to their respective values for healthy and/or diseased subjects to determine the health status of the subject.

For example, one aspect of the present invention relates to methods and devices for detecting the presence or risk of acquiring a disease or condition as related to differential solubility behavior of a plurality of species in the aqueous portions of two substantially immiscible liquids. Aqueous partitioning systems may be generally employed in some embodiments, wherein the partitioning behavior of at least two species is determined, e.g., to be different between healthy subjects and subjects having a disease or condition.

Figure 1:
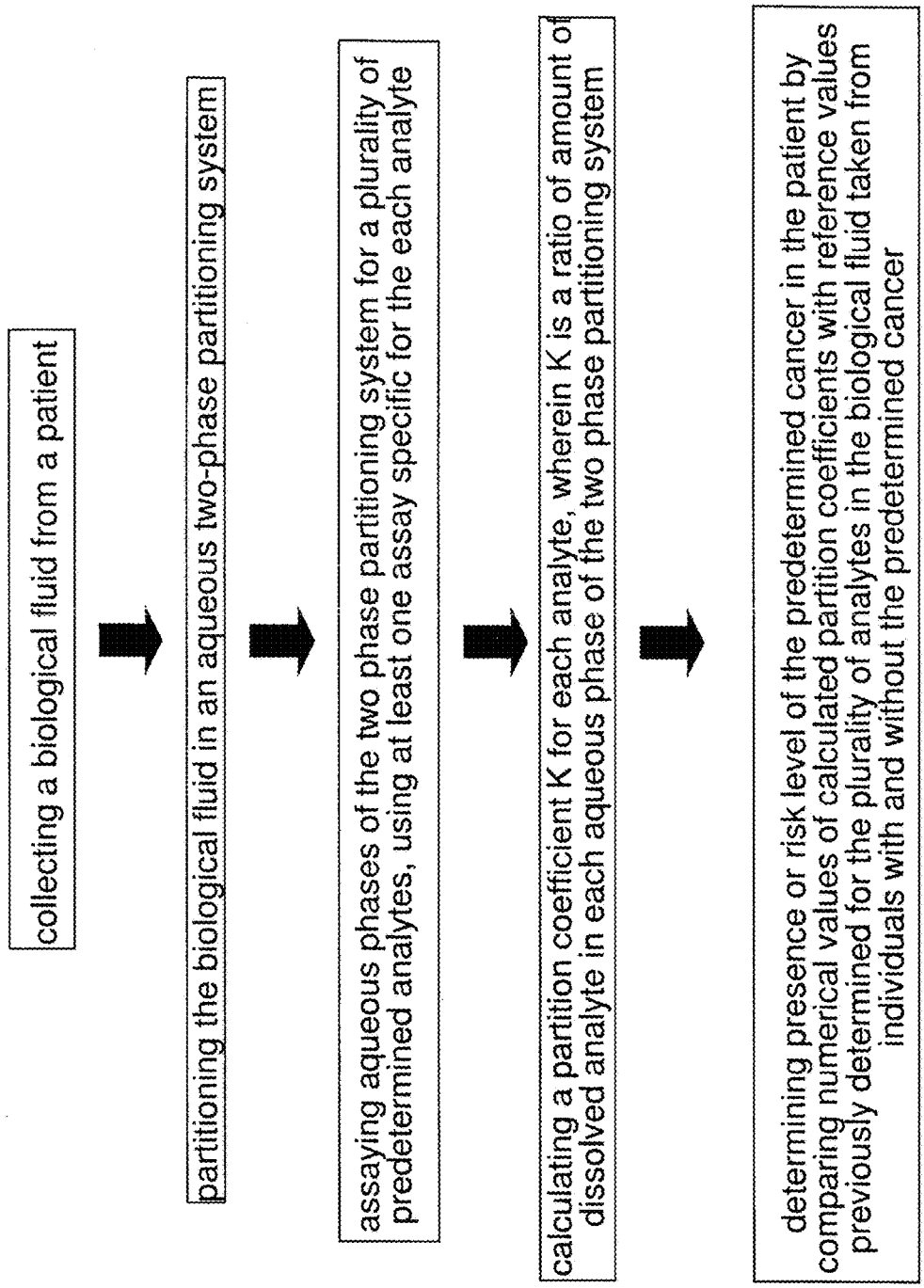
FIG. 1 shows a flowchart related to a method of one embodiment of the invention.
Figure 3:
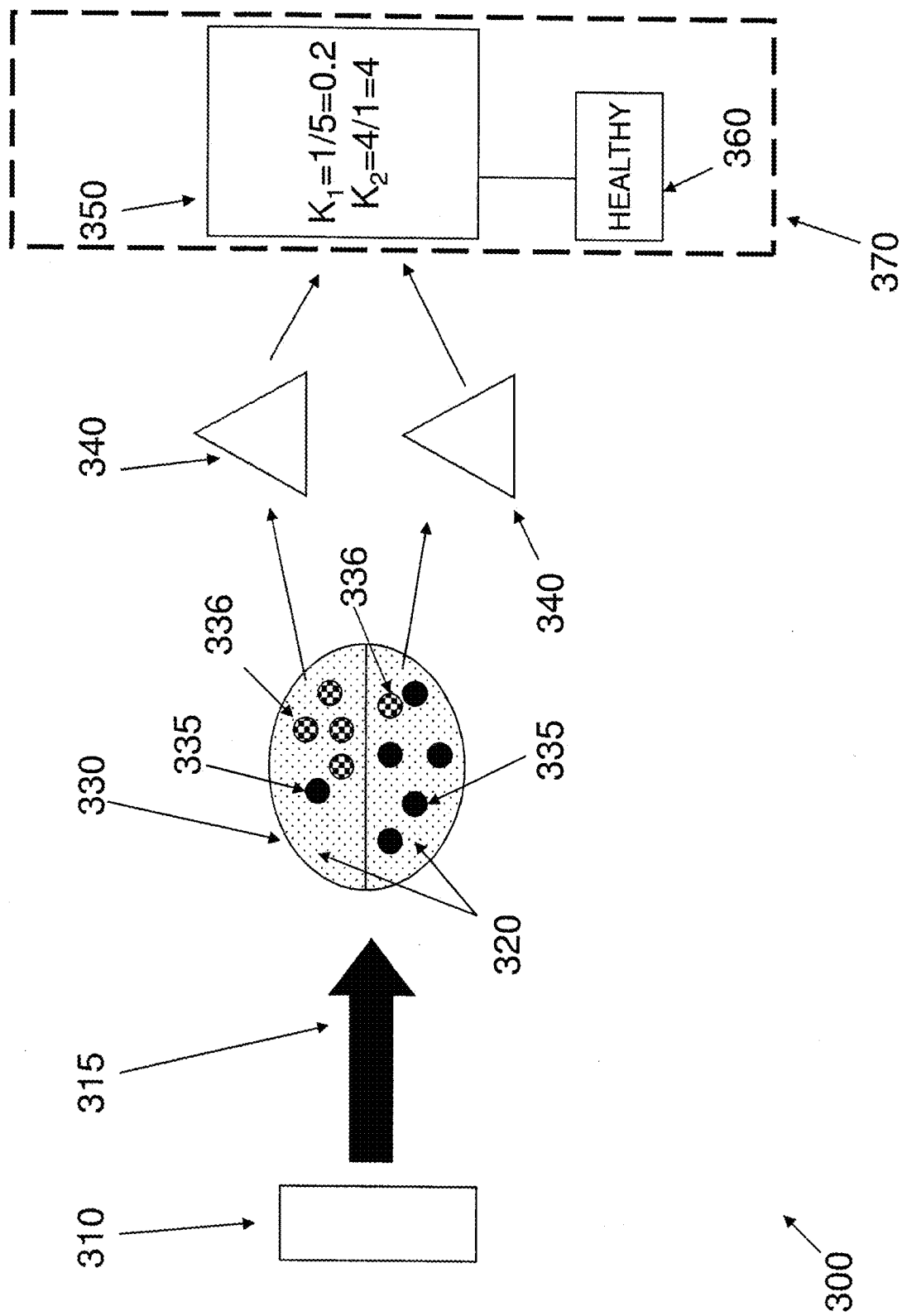
FIG. 3 shows a schematic view of yet another embodiment of the invention.

For purposes of better understanding some embodiments of the present invention, as illustrated in FIGS. 1-3 of the drawings, reference is first made to FIG. 1. This figure shows a flowchart of an embodiment of the instant invention for diagnosing or determining a cancer, e.g., one that is predetermined. As shown in this figure, the embodiment includes: collecting a biological fluid from a subject (which may contain a mixture of species); partitioning the biological fluid in an aqueous two-phase (or multi-phase) partitioning system; assaying one or more of the aqueous phases of the two-phase partitioning system for a plurality of species, using one or more assays to determine the species; calculating a partition coefficient K for each species, wherein K is a ratio of amount of dissolved species in each aqueous phase of the two-phase partitioning system; and, determining the health status of the subject. For example, the presence or risk level of a disease or condition (e.g., cancer) in the subject may be determined by comparing numerical values of the calculated partition coefficients with reference values previously determined for the plurality of species in the biological fluid taken from subjects with and without the disease or condition. In some cases, the biological fluid tested may include fluids such as whole blood, blood serum, blood plasma, saliva, urine, CNS fluid, breast nipple aspirate fluid, cerebral spinal fluid, semen, or the like. The biological fluid may also be collected from a subject, and may in some cases be processed for further use. Specific species can be determined in the biological fluid. These species may come from a variety of cellular sources and their specific functions or identities may be known or even unknown in some cases.

In some embodiments, the species can be partitioned in the aqueous phases of two (or more) substantially immiscible liquids of a partitioning system, wherein each species is dissolved in each aqueous phase, and wherein the dissolution of the species is generally related to the presence or absence of the specific disease or other condition under diagnosis. For example, the species may include various biomarkers for cancer or other diseases. The two aqueous-based solvent phases of the partitioning system may have different molecular structures in some cases. In equilibrium, differences between the molecular interactions of any dissolved molecule and the solvents in the various phases may be determined using the value of a partitioning coefficient between the phases. The value of the partition coefficient for a species may change, for instance, if the three-dimensional structure of the species changes, e.g., as a function of the presence of cancer or other disease, or other differences between a healthy subject and a subject with a disease or condition, etc. Thus, for example, a species that is primarily dissolved in one phase when a healthy subject is tested may be found to be mostly dissolved in a different phase for a subject that has a disease or other condition.

Thus, for example, a cancerous growth may lead to a change in the three-dimensional structure of a species, which can be determined as noted above. Accordingly, by determining the partitioning of a plurality of one, two, or more species, and optionally by partitioning such species versus a control or reference, any changes in the species may be determined. In some cases, such changes may be determined even if the specific change in the species (for example, to a different configurational state) is not known. In some embodiments of the present invention, even the identity of one or more species may not necessarily be known.

For example, one set of embodiments is generally directed to a method that makes use of changes in the partitioning behavior of a plurality of species in response to the presence or susceptibility towards a specific cancer (or other disease or condition). The changes in solubility behavior may be related to changes in the structure of the species, and/or changes in structure of the species may be related to the cancer-associated metabolic behavior.

The chemical ingredients used to prepare an aqueous system that naturally partitions into two or more phases may be selected (e.g., as discussed below) so as to provide this differentiation of solubility behavior as a function of presence or absence of cancer in a subject. Once one or more of the species have been partitioned, the species in each phase can be assayed, for example, through immuno-specific assays like ELISA. Each of the partitioned species is assigned a concentration value for each phase. A partitioning coefficient, K, may also be determined in some cases from the ratio of concentration of species in each phase.

K values for each species (e.g., for subjects with different health statuses, e.g., healthy and diseased subjects) may, in some embodiments, be chosen to be significantly different. For example, K values determined for a subject may be compared to similar ratio values previously determined and recorded for subjects with known health statuses. The K value may be compared to values associated with healthy subjects and/or values for those known to have a disease or condition, or have a predisposition to a disease or condition (for example, the subject may have a cancer of interest, or a high risk factor for it). The number of species analyzed may be selected under certain conditions to allow for the greatest discrimination between various health statuses (for example, healthy versus diseased), e.g., commensurate with cost, speed and other operational parameters. Additionally, in some embodiments, the partitioning system may be selected in certain embodiments to allow for large K differences between various health statuses (for example, healthy versus diseased).

In some (but not all) embodiments, while the specific species may be known a priori, e.g., so as to identify and quantify them, their specific biological purposes or functions may not necessarily be known. Even if unknown, various methods such as those described herein may still be performed by those of ordinary skill in the art. Thus, for example, cancer identification may be made by simultaneously analyzing the solubility behavior of various species using the same partitioning system, even if, in some cases, the specific relationship with the cancer under investigation is unknown. Such a state of affairs allows for greater flexibility for cancer detection, as the main factor of interest is change in partitioning behavior in the liquid partitioning system as a function of health status (for example, the absence or presence of cancer in a subject, the predisposition of a subject to cancer, or the like). In addition, while immunoassays can be employed for quantification of various species in one or more of the aqueous phases, other methodologies may be employed in other embodiments.

According to certain embodiments, while prior art inventions describe the portioning of single biomarkers for detection of disease, it is unexpected that one could create a single partitioning system that would successfully allow for altered partitioning behavior for two or more species as a function of health status, such as a disease or condition.

Attention is now turned to FIG. 2, which shows a flowchart for a method according to another embodiment of the instant invention. In one set of embodiments, a method of the invention includes: collecting a biological fluid from a subject (which may contain a mixture of species); partitioning the biological fluid in at least one aqueous two-phase (or multi-phase) partitioning system; assaying one or more of the aqueous phases of the aqueous two-phase partitioning system for a plurality of species, using at least one assay specific for the each species; determining the concentration for one or more species in one or more phases; and determining the health status of the subject. For example, the presence or risk level of the disease or condition in the subject may be determined by comparing the concentrations of the species to known concentration values in corresponding aqueous phases derived from biological fluid samples taken from subjects having various health statuses (e.g., subjects with and without the disease or condition, subjects who are predisposed and who are not predisposed to the disease or condition, or the like). In some cases, this can be used for detection of or determination of a disease or condition via a traditional blood sample, urine sample or the like, as examples of suitable biological fluids. In certain embodiments, this can be used for detection of or determination of risk for a specific disease or condition via testing of biological fluids such as blood, urine, semen or the like. The biological fluid may be collected from a subject, and may be processed for further use. Specific species such as biomolecules can be detected in the biological fluid in some cases. These species may come from a variety of cellular sources, and their specific functions may even be unknown in some cases.

In one set of embodiments, the species may be partitioned in the aqueous phases of two or more substantially immiscible liquids, wherein each species is differentially dissolved in each aqueous phase. The differential dissolution behavior may in some cases be related to the presence or absence of the specific disease or condition under diagnosis. The aqueous solvent phases may have different molecular structures. In equilibrium, the differences between the molecular interactions of a species and the solvents in the various phases may be manifested through differential solubility of the species between the phases.

In some embodiments, only one of the aqueous phases is analyzed for concentration, for each species; no ratio calculation may be used, as the second aqueous phase is used for partitioning but not for the assay (however, in other embodiments, more than one of the aqueous phases may be analyzed for species concentrations, as discussed herein). Thus, a species that shows a high concentration in one phase when a healthy subject is tested may be found to have a significantly lower concentration in a subject having or at risk of a disease or condition, which may lead to a change in the three-dimensional structure of the species. Thus, sampling only one phase may either show the corresponding decrease or increase in concentration for each species of interest.

Diseases and conditions that may be tested as discussed herein include, but are not limited to, cancers, hereditary diseases, bacterial infections, viral infections, and sepsis.

Preparation of partitioning systems such as those described herein may, in some embodiments, include large-scale robotic screening of chemical ingredients such as soluble polymers, salts, and other additives to cause spontaneous phase separation, e.g., into two or more phases. This screening may be targeted to discover and/or optimize such formulae to distinguish those which could confer differential partitioning of two or more species from samples of subjects with various health statuses. For example, the species may be isolated from healthy samples, and from those who have a disease or other condition. Thus, once a solvent system of at least two substantially immiscible liquid layers is defined via the composition of its starting chemical ingredients, the relevant species from subjects of unknown health conditions may, in certain cases, also be partitioned, assayed, and analyzed. In some embodiments, the concentration of species in one phase, and not its concentration ratio between phases, may be used for determination of a disease or condition in a subject.

It is noted that the specific species used in the analysis of a disease or condition may be predetermined in some embodiments (for example, to allow for analysis of concentration values from healthy subjects and subjects with a disease or condition). The specific species may or may not be directly related to the disease or condition. For example, changes in solubility behavior as related to changes in single phase concentration values between healthy subjects and subjects with a disease or condition may be a direct or indirect outcome of the presence of the disease or condition. For the latter, for example, a human protein may be bound up with a bacterial ligand produced by a disease-causing bacteria, or the three dimensional structure of the protein-ligand may be significantly different than the corresponding structure (and/or charge) of the protein alone, etc. As a result, the protein dissolution profile may change as a function of disease presence, with a resulting change in concentration value for this specific species. Accordingly, in certain embodiments of the invention, a disease or condition such as an infection may be determined.

Attention is now turned to FIG. 3, which shows yet another embodiment of the instant invention. The components of a device associated with the disease detection system 300 include the following: a unit 310 for collecting a biological fluid 315 from a subject; at least one aqueous two-phase partitioning system 320, a unit 330 for partitioning a portion of a biological fluid of interest in the two-phase partitioning system; a plurality of assays 340 for determining the concentrations of a plurality of species (335, 336) in aqueous phases of the two-phase partitioning system 320; a computing element 350 adapted to determine a portioning coefficient K for each species, wherein K represents the distribution of each species 335, 336 in the aqueous portions 330 of the two-phase partitioning system 320; and, a determination element 360 adapted to compare the coefficient K with known values of K for samples of healthy subjects and subjects with a disease or condition (or at risk for the disease or condition). In this example, there are two relevant species 335, 336 whose respective K values are 1/5=0.2 and 4/1=4 as reflected in their presence in the aqueous phases of the two-phase portioning system 320 (K=[x]top/[x]bottom). It should be understood, of course, that these values are meant to be merely illustrative and not limiting.

It should also be understood that all of the elements described here may be included in a single unit or a small number of components (e.g., modular components). The elements are shown individually here so as to aid in the understanding of the present invention, but should not be seen as limiting. As shown here, computing element 350 and determination element 360 may generally be associated with a computing device 370 that may further include a controller element (not shown) that directs various tasks from the receipt of biological fluids to producing a final determination of disease presence. Computing device 370 may be realized as any relevant device and includes but is not limited to computers, hand-held computers, tablet computers, cellular phones, laptop computers, and tabletop computers.

In some aspects, a feature for allowing differential solubility for the species is the liquid partitioning system. Thus, certain embodiments of the invention make use of a liquid partitioning system for use in the detection of a disease or condition in a subject, including: two or more liquid phases, the liquid phases being substantially immiscible, wherein each liquid phase has an aqueous component wherein a plurality of species associated with the disease or condition can be solubilized, and wherein the concentrations of the species in the liquid phases may be related to the presence or absence of the disease or condition in the subject.

Typical, but non-limiting, components of the aqueous phases include at least one of polyethylene glycol, dextran, polyvinyleperrolidone, Ficoll®, and copolymer of ethylene glycol and propylene glycol. The liquid partitioning system may include, in some embodiments, substantially immiscible layers which some or all have an aqueous component. The species may interact differently with the chemicals (and water) of each layer, and thus dissolve differentially as shown in the FIG. 3. Liquid partitioning systems, including aqueous liquid partitioning systems and various compositions for forming such systems, are discussed in greater detail below. However it should be noted that the invention is not limited to only liquid-liquid partitioning, e.g., as described above, but also encompasses, in other embodiments, chromatography (e.g., liquid-liquid partition chromatography), heterogeneous two-phase systems, or multi-phase heterogeneous systems), and other suitable techniques for generating a partition coefficient or at least an apparent partition coefficient.

In addition, in accordance with certain aspects of the present invention, the state of a molecule, such as a species, can be affected by many different factors including, but not limited to, changes in the chemical structure of the species (e.g., addition, deletion or substitution of amino acids in proteins, covalent modification by chemical agents or cleavage by chemical or thermal degradation, addition or deletion of carbohydrates to the structure, etc.), interactions with one or more other biomolecules or ligands, and the like. Evaluation of different states can be used as one method of determining the potential effectiveness of different potential species, condition of the potential species, condition or state of an environment (e.g., a mixture of species) within which the species reside, and the like.

As mentioned above the present invention involves, in certain aspects, the investigation of the state of species. In one set of embodiments, one or more of the species is a biomolecule, although the invention is not limited to only biomolecules. Other embodiments of the present invention can be applied to essentially any molecular species and/or interaction, whether biological, biochemical, chemical, or other species, and those of ordinary skill in the art will understand how the invention can be used in the context of non-biological molecules. Accordingly, it is to be understood that whenever "biomolecules" is used in the description of the invention, any non-biological molecule also can be used or studied as a species.

Thus, in one aspect, the present invention involves, in some embodiments, techniques for determining information about the composition of a mixture of two or more species (such as biomolecules) and/or molecules which interact with species (such as biomolecules). The mixture may originate from a biological fluid (or other sample), such as a human clinical sample or other biological fluid, tissue, cells, a subject, etc., or the mixture may be a synthetic mixture. The mixture can come from a biological system (e.g., a subject) which includes, but is not limited to, a human or non-human mammal. Non-human mammals include, but are not limited to, a dog, cat, horse, cow, pig, sheep, goat, chicken, primate, rat, and mouse, or a bacteria, virus, fungus, or of plant origin.

The invention also relates, in some embodiments, to developing and determining characteristics (quantitative and/or qualitative) of a mixture that are obtained, for example, via processing using multi-phase partitioning, which can reflect certain structural and functional characteristics of biomolecules or molecules that interact with biomolecules in the original mixture. These characteristics can be used, for example, for establishing relationships between the composition of the mixture and the physiological state of the biological source of the mixture e.g., the state of health or disease of a subject. These characteristics can also be used to design experimental conditions for subsequent fractionation of the mixtures into subsets enriched in the molecule(s) of interest for the purpose of the analysis, while simultaneously reduced in the total number of different molecule(s) in some cases. The systems and methods of the present invention can also be useful for detecting, classifying, and/or predicting changes in a mixture of biomolecules or molecules that interact with biomolecules. For example, the mixture may be a synthetic mixture, or a mixture associated with a particular disease or physiological state of a living organism, cells, tissues, or biological liquids. The systems and methods of the present invention can also be used to detect changes to a set of biomolecules in a biological mixture and these changes could further be used to detect and classify a diagnostic that is related to such changes.

Examples of such changes in a mixture can be the differences in a property of a species of the mixture, such as its conformation, structure and/or interaction tendency with respect to another molecule or molecules (e.g., its binding affinity or other interaction characteristic with respect to another molecule or molecules). For example, if the mixture includes proteins or other biomolecules, such changes may be induced through primary sequence modification, by degradation of the proteins or other biomolecules through chemical, thermal, or other degradation mechanisms, by interaction with other molecules and/or biomolecules, by interaction with low molecular weight compounds (e.g., hormones, peptides, vitamins, cofactors, etc.), by changes in the relative content or concentration of the constituents of the mixture, by reactions such as enzymatic reactions, etc. The systems and methods of the present invention can be used, in some cases, to detect, analyze and/or characterize biological materials, including but not limited to, polypeptides, proteins, carbohydrates, nucleic acids, polynucleotides, lipids, sterols, and mixtures or derivatives thereof, e.g., for the purpose of detection of, or onset of, a particular disease or physiological state, monitoring its progress, treatment, etc.

Comparison and classification steps involved in the invention can make use of additional information not necessarily related to (not directly derived from) the analytical methods of the invention. For example, blood pressure, temperature, blood glucose level, and/or essentially any other measurable physiological condition can be used in conjunction with various techniques of the invention to analyze one or more diseases or conditions.

It will be recognized by those of ordinary skill in the art that these biological materials can be found in any suitable form, for example, in the form of extracts from natural sources, biological liquids, collections of molecules generated by combinatorial chemical or biochemical techniques and combinations thereof, synthetically created, etc. In one set of embodiments, the biological materials arise from a biological fluid (e.g., withdrawn from a subject), and such biological materials may include one or more species (e.g., present as a mixture).

In one embodiment, the present invention provides a method to determine certain conditions under which variations among samples representing different species (or mixtures of species) could be detected, i.e., determining a set of criteria and/or system components as a "tool," or a part of a tool, to determine information, as well as the subsequent use of the tool. For example, the ability of a system to determine a partition coefficient or a relative measure of interaction between a species and one or more interacting components that can define one or more phases of the system can serve as an important tool or component of such a tool. Specifically, as one example, the partitioning of the constituents of a sample between two phases having different chemical or biochemical affinities or other characteristics, such as solvent structures, may separate the constituents by their relative affinity for media of different properties or composition. This separation technique thus can include or, alternatively, can be unlike those typically used in proteomics or similar techniques, e.g., 2-D gel electrophoresis, in which charge and size differences are the two dimensions used to separate the constituents of a sample. In some cases, e.g., for many applications in proteomics, the present invention provides the ability for performing sequential or serial partitioning, with either the same of different conditions, which may result in additional amplification of differences in the fractionated samples. These fractions may be further analyzed using standard proteomics techniques.

As mentioned elsewhere herein, aqueous multi-phase (e.g., two-phase) partitioning systems are well-suited for use in many or most embodiments of the invention, but other partitioning systems can be used. Where terms such as "aqueous two-phase partitioning" or "aqueous multi-phase partitioning" is used, it is to be understood that other systems can be used. Partitioning of a biopolymer in aqueous two-phase systems may depend on its three-dimensional structure, type and topography of chemical groups exposed to the solvent, etc. Changes in the 3-D structure of a receptor induced by some effect, e.g., by binding of a ligand binding or by structural degradation, also can change the topography of solvent accessible chemical groups in the biomolecule, or both the topography and the type of the groups accessible to solvent. One result of these changes may be an alteration in the partition behavior of the biomolecule or other species.

Biomolecules or other species can be determined to diagnose or determine an underlying physiological condition or disease. Rapid and specific quantification techniques are readily available to those of ordinary skill in the art which can be used to quantify the concentration of biomolecules using standard methods and techniques directly in the biological sample, e.g., using antibodies in an Enzyme Linked ImmunoSorbent Assay (ELISA). The concentrations in the two interacting components of each system can be used to calculate the values of the partition coefficients. Changes to the individual values of the partition coefficients thus may indicate certain changes to the biomolecules. In some cases, the change to the partition coefficient of one or more biomolecules, can result in a definitive diagnosis of a disease or condition. In yet other cases, partitioning of the samples in multiple systems and performing the steps above, then observing the pattern of values for one or more biomolecules, can provide an alternative way to constructing a sensitive and specific diagnostics method.

Thus, for example, a mixture of biomolecules may be obtained from a subject, and partitioned in one or more aqueous two-phase (or multi-phase) partitioning systems. Partition coefficients for one or more of the biomolecules may be determined, and used to determine a physiological condition of the subject, e.g., determining the presence or risk level of the cancer in the subject. In some cases, the partition coefficients may be compared to reference partition coefficients, e.g., reference values previously determined for biomolecules taken from subjects with and without a disease or condition, e.g., cancer.

For example, in connection with certain aspects of the invention, a variety of studies can take place. For example, the studies may include determining analysis procedures that involve taking samples from a single subject or multiple subjects. In one embodiment, a positive sample and a control sample can be taken from a single subject. For example, a subject may have a tumor and a positive sample may be a portion of the tumor, where a control sample is from a non-tumorous portion of the subject. The samples, both positive and control, can be taken from the subject at the same time or at different times. For example, samples from a tumorous portion of a subject can be taken at different times, and used to determine differences in one or more biomolecules, e.g., to analyze the progression of a tumor.

Similarly, such changes may be detected using other systems and methods which have an underlying dependence upon the topography and/or the types of solvent accessible groups. Examples of such other methods include, but are not limited to, column liquid-liquid partition chromatography (LLPC), a heterogeneous two-phase system, or a multiphase heterogeneous system. In some cases, an apparent partition coefficient may be generated that expresses the relative changes in the average partitioning between a first and a second phase. For example, in LLPC, the retention volume of a receptor may be used as the apparent partition coefficient.

As previously discussed, aqueous two-phase partitioning systems may be used in various aspects of the invention to determine one or more biomolecules (or other species). For instance, the partition coefficients of one or more biomolecules may be studied within an aqueous two-phase partitioning system, e.g., by determining the amount and/or concentration of the biomolecules in each of the phases using techniques such as those described herein.

Aqueous two-phase systems are well-known to those of ordinary skill in the art, and can arise in aqueous mixtures of different water-soluble polymers or a single polymer and a specific salt. When two or more certain polymers, e.g., dextran ("Dex") and polyethylene glycol ("PEG"), or one or more certain polymers and one or more inorganic salts, e.g. polyvinylpyrrolidone ("PVP") and sodium sulfate, are mixed in water above certain concentrations, the mixture can separate into two (or more) immiscible aqueous phases under certain conditions. There may be, in certain instances, a discrete interfacial boundary separating any two phases, for example, such that one is rich in one polymer and the other phase is rich in the other polymer or the inorganic salt. The aqueous solvent in one or both phases may provide a medium suitable for biological products. Two-phase systems can also be generalized to multiple phase system by using different chemical components, and aqueous systems with a dozen or more phases are known in the art and can be used in connection with the invention.

When a species is introduced into such a two-phase system, it may distribute between the two phases. In this and other systems, the species can be found at different concentrations within each phase, or can be at the same concentration within each phase. Partitioning of a solute can be characterized by the partition coefficient "K," defined as the ratio between the concentrations of the solute the two immiscible phases at equilibrium. It has previously been shown that phase separation in aqueous polymer systems may result from different effects of two polymers (or a single polymer and a salt) on the water structure (B. Zavlaysky, *Aqueous Two-Phase Partitioning: Physical Chemistry and Bioanalytical Applications*, Marcel Dekker, New York, 1995). As the result of the different effects on water structure, the solvent features of aqueous media in the coexisting phases can differ from one another. The difference between phases may be demonstrated by techniques such as dielectric, solvatochromic, potentiometric, and/or partition measurements.

The basic rules of solute partitioning in aqueous two-phase systems have been shown to be similar to those in water-organic solvent systems (which can also be used as systems in the present invention). However, what differences do exist in the properties of the two phases in aqueous polymer systems are often very small, relative to those observed in water-organic solvent systems, as would be expected for a pair of solvents of the same (aqueous) nature. The small differences between the solvent features of the phases in aqueous two-phase or multi-phase systems can be modified so as to amplify the observed partitioning that results when certain structural features are present.

It is known that the polymer and salt compositions of each of the phases usually depend upon the total polymer and/or salt composition of an aqueous two-phase system. The polymer and/or salt composition of a given phase, in turn, usually governs the solvent features of the aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media may govern the sensitivity of a given aqueous two-phase system toward a particular type of solvent accessible chemical groups in the receptor. This sensitivity, type, and topography of the solvent accessible groups in two different proteins, for example, can determine the possibility of separating proteins in a given aqueous two-phase system.

In some cases, a particularly sensitive system may be required, i.e., a system that is very sensitive to, and able to determine a partition coefficient or a relative measures of interaction with respect to, two very similar species. This sensitivity may be of importance when, for example, subtle differences are being detected between the conformational changes in a receptor induced by binding of closely related chemical compounds. The present invention provides, in one set of embodiments, efficient and successful systems and methods for screening aqueous phase compositions to identify and/or amplify differences between the compositions of two mixtures. By utilizing a wide variety of different conditions to screen each molecule, as described herein, different partitioning behavior may be obtained reliably without the need to fully understand the underlying theory of aqueous two-phase partitioning, or any of the other related or substitutable techniques.

Biomolecules such as proteins, nucleic acids, etc. may be distributed between the two or more phases when placed into such a system. For example, in the case where phase-forming polymers are used, solutions comprising one or more of the two polymers and the biomolecule may be mixed together such that both phase-forming polymers and the biomolecule are mixed. The resulting solution is resolved and a two-phase system is formed. Optionally, centrifugation can be used to enhance separation of the phases. It will be recognized by those of ordinary skill in the art that partitioning behavior of a biomolecule may be influenced by many variables, such as the pH, the polymers used, the salts used, factors relating to the composition of the system, as well as other factors such as temperature, volume, etc. Optimization of these factors for desired effects can be accomplished by routine practice by those of ordinary skill in the relevant arts, in combination with the current disclosure.

Evaluation of data from partitioning of a biomolecule or other species can involve use of the partition coefficient, in some embodiments of the invention. For example, the partition coefficient of a protein can be taken as the ratio of the protein in first phase to that in the second phase in a biphasic system. When multiple phase systems are formed, there can be multiple independent partition coefficients, each of which can be defined between any two phases. It will be recognized that the partition coefficient for a given biomolecule of a given conformation will be a constant if the conditions and the composition of the two-phase system to which it is subjected remain constant. Thus, if changes are observed in the partition coefficient for a protein upon addition of a potential binding partner, these changes can be presumed to result from changes in the protein structure caused by formation of a protein-binding partner complex. The partition coefficient K, as used herein, is a specifically mathematically defined quantity as further described herein, and the term includes coefficients representing the relative measure of interaction between a species and at least two interacting components. It should also be recognized that differences between partition coefficients of corresponding species in two or more mixtures could indicate, in addition to potential structural changes, also binding or lack of binding of such species to other species in the mixtures.

In a non-limiting example of one partitioning system, aqueous multi-phase systems are known to be formable from a variety of substances. For example, in order to determine the partition coefficient of a protein (or a mixture of a protein with another compound) to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, and the protein mixture can be mixed in the amounts and conditions (e.g., pH from about 3.0 to about 9.0, temperature from about 4° C. to 60° C., salt concentration from 0.001 to 5 mol/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 g to 4000 g, or higher. Aliquots of each settled (resolved) phase can be withdrawn from the upper and/or lower phases (or from one or more phases, if multiple phases are present). The concentration of species within the phases can be determined for one or more of the phases.

Different assay methods may be used to determine partition coefficients between a species and interacting components, e.g. in the form of the concentration of the biomolecules in each phase of a multi-phase system. The assays will often depend upon the identity and type of species or other biomolecule present. Examples of suitable assay techniques include, but are not limited to, spectroscopic, immunochemical, chemical, fluorescent, radiological and enzymatic assays. When the biomolecule is a peptide or protein, the common peptide or protein detection techniques can be used. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents. Alternatively, if the protein is either an antibody or an antigen, certain immunochemical assays can be used in some cases.

The concentration of the species in each phase can be used to determine the partition coefficient of the sample under the particular system conditions. Since the partition coefficient reflects the ratio of the two concentrations, the absolute values are not typically required. It will be recognized that this can allow certain analytical procedures to be simplified, e.g., calibration can be eliminated in some instances. It also may have significant advantage for negating the effect of natural variability in the absolute concentration of proteins in samples obtained from, e.g., various subjects, when comparing two or more samples, thus focusing on those changes detected as differences in the partition coefficient relevant to changes to the structure of the individual species in the samples.

It should be recognized by those skilled in the art that the steps in above description of obtaining the partition coefficient could be substituted by other steps or measurements. Depending on the size, volumes, amount of the biomolecule, detection system, discrete or continuous operation using either liquid-liquid or liquid-solid portioning, other processes that effectively result in results described herein could be developed. Such modifications and different processes should not limit the scope of this complete invention.

The partition coefficient can then be compared with other partition coefficients. For example, a partition coefficient for a species can be compared to the partition coefficients for the species under different conditions, a partition coefficient for a species can be compared to the partition coefficients for the species when combined with other species, a set of partition coefficients for a species can be compared to other sets of partition coefficients, etc. This comparative information can be obtained at the same time or near the same time and in the same system or a similar system as is used to determine the interaction characteristics of the molecules of interest, or can be provided as pre-prepared data in the form of charts, tables, or electronically stored information (available on the Internet, disc, etc.)

In one embodiment of the present invention, proteins or other biomolecular mixtures from an experimental sample and from a reference sample (determined simultaneously, previously, or subsequently, as described above) may be caused to partition in a variety of different aqueous two-phase systems, e.g. formed by different types of polymers, such as Dextran and PEG or Dextran and Ficoll®, by the same types of polymers with different molecular weights, such as Dextran-70 and PEG-600 or Dextran-70 and PEG-8,000, by the same polymers but containing different in type and/or concentration salt additives, different buffers of different pH and concentration, etc. The overall partition coefficients for the mixtures determined using a particular assay procedure (e.g., same for both samples) can be determined in all of the systems. In one embodiment, the systems displaying different partition coefficients for the mixtures under comparison may be selected as a separation medium, for example, for further fractionation and/or characterization of the mixtures. In another embodiment, mixtures are partitioned using one or more standard systems with known properties, e.g., those providing enhanced sensitivity levels towards hydrophobic or ionic interactions. In such a case, the individual partition coefficients of the species comprising the mixtures may be determined following separation of the mixtures in the phases and/or compared between two or more mixtures.

The reasons for the observed differences in the partition behavior of the two samples do not have to be scientifically characterized for such differences to be useful for many applications, e.g., for diagnostics. Such differences, resulting in partitioning behavior, may arise due to multiple reasons, including relative compositional, structural, or conformational differences in the samples when exposed to aqueous media of different solvent structures.

In some embodiments, one or more of the fluid manipulations may occur within a microfluidics device. "Microfluidic," as used herein, refers to a device, article, or system including at least one fluid channel having a cross-sectional dimension of less than about 1 mm. The "cross-sectional dimension" of the channel is measured perpendicular to the direction of net fluid flow within the channel. Thus, for example, some or all of the fluid channels in an article can have a maximum cross-sectional dimension less than about 2 mm, and in certain cases, less than about 1 mm. In one set of embodiments, all fluid channels in an article are microfluidic and/or have a largest cross sectional dimension of no more than about 2 mm or about 1 mm. In certain embodiments, the fluid channels may be formed in part by a single component (e.g. an etched substrate or molded unit). Of course, larger channels, tubes, chambers, reservoirs, etc. can be used to manipulate in other embodiments of the invention. In one set of embodiments, the maximum cross-sectional dimension of the channels in an article is less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. In some cases, suitable microfluidics devices may be readily obtained commercially.

In addition, according to some aspects of the present invention, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific example of a technique that can make use of a computer or other automated system is in a process in which a physiological condition of a system as determined by determining a relative measure of interaction between one or more species from a sample from the system and various interacting components of a partitioning system. In the clinical setting, this may be accomplished by drawing a sample of blood (milliliter-sized or a very small sample such as a drop or less) and subjecting the blood sample or a subset thereof (e.g., plasma) to a multi-phase partitioning process. The results of this process can then be compared to similar behavior of markers in a similar system, which can take the form of data stored electronically.

Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent.

"Partitioning system," as used herein, refers to any material having at least two phases, sections, areas, components, or the like, at least two of which can interact differently with at least one species to which they are exposed. For example, a partitioning system can include different areas of a solid surface, which can interact differently with a particular molecule exposed to the different sections, a multi-phase system such as a multi-phase liquid system, e.g., an aqueous/non-aqueous system or an aqueous multi-phase system (as defined herein) to which one or more species can be exposed and optionally dissolved, at least some of which species can interact differently with different phases. For example, a particular species may have a greater affinity for one phase rather than another phase to the extent that a multi-phase partitioning system can isolate a species from a mixture, or cause a species to partition at least in some way differently between the phases.

"Aqueous multi-phase system," as used herein, refers to an aqueous system which includes greater than one aqueous phase in which a species can reside, and which can be used to characterize the structural state of the species according to the methods described herein. For example, an aqueous multi-phase system can separate at equilibrium into two, three, or more immiscible phases. Aqueous multi-phase systems are known in the art and this phrase, as used herein, is not meant to be inconsistent with accepted meaning in the art. Examples of various aqueous multi-phase systems, and their compositions, are discussed herein.

An "interacting component" means a component, such as a phase of multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination thereof. A set of interacting components can form a system useful in and in part defining any experimental method which is used to characterize the structural state of a species according to the methods described herein. Typically, a system of interacting components can measure the relative interaction between the species and at least two interacting components. An aqueous multi-phase system is an example of a system of interacting components, and it is to be understood that where "aqueous system" or "aqueous multi-phase system" is used herein, this is by way of example only, and any suitable system of interacting components can be used.

Where aqueous two-phase and aqueous multi-phase systems are described herein, it is to be understood that other systems, as used herein, systems analogous to those comprising only aqueous solutions or suspensions can be used. For example, an aqueous two-phase system can include non-aqueous components in one or more phases that are not liquid in character. In this aspect, multi-phase systems also refers to related techniques that rely on differential affinity of the biomolecule to one media versus another, wherein the transport of the biomolecule between one medium and, optionally, another medium occurs in an aqueous environment. Examples of such multi-phase systems include, but are not limited to, HPLC columns or systems for liquid-liquid partition chromatography, as are known to those of ordinary skill in the art.

"Relative measure of interaction," with reference to a particular species as used herein, means the degree to which the species interacts with another species or with a phase of a multi-phase system in a relative sense. For example, a particular species may have a greater affinity for one phase of a multi-phase system rather than another phase or phases, the degree to which it interacts with or resides in, that phase as opposed to other phases defines its relative measure of interaction. Relative measures of interaction, in the context of the present invention, are generally determined in a ratiometric manner, rather than an absolute manner. That is, where a species can interact with each phase of a two-phase system but resides more preferably in one than the other, the present invention typically makes use of information as to the ratio of concentration of the species in each of the two phases, but not necessarily of the absolute concentration of the species in either phase. In other cases, the interaction can be an interaction based not upon residence of a particular species within a particular solvent or fluid carrier, but interaction with a solid surface such as a solid phase of a chromatography column where the relative measure manifests itself in elution time, or can involve geometric or spatial interaction such as a particular species interaction with a porous substrate as opposed to that of a different species or a different substrate.

"Partition coefficient," as used herein, refers to the coefficient which is defined by the ratio of chemical activity or the concentrations of a species in two or more phases of a multi-phase system at equilibrium. For example, the partition coefficient (K) of a species in a two-phase system can be defined as the ratio of the concentration of species in the first phase to that in the second phase. For multi-phase systems, there can be multiple partition coefficients, where each partition coefficient defines the ratio of species in first selected phase and a second selected phase. It will be recognized that the total number of partition coefficients in any multi-phase system will be equal to the total number of phases minus one.

For heterogeneous phase systems, an "apparent partition coefficient," as used herein, refers to a coefficient which describes information obtained from alternative techniques that is correlated to the relative partitioning between phases. For example, if the heterogeneous two-phase system used is an HPLC column, this "apparent partition coefficient" can be the relative retention time for the species. It will be recognized by those of ordinary skill in the art that the retention time of a species, in such a case, reflects the average partitioning of the species between a first, mobile phase and a second, immobile phase. Also, it will be recognized that other, similarly determinable properties of species can also be used to quantify differences in physical properties of the species (e.g. in other techniques) and are, therefore, suitable for use as apparent partition coefficients.

"Bind," as used herein, means the well-understood receptor/ligand binding, as well as other nonrandom association between a biomolecule and its binding partner. "Specifically bind," as used herein, describes a binding partner or other ligand that does not cross react substantially with any biomolecule other than the biomolecule or biomolecules specified. Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Molecule-molecule interaction," such as biomolecule-biomolecule interaction, protein-protein interaction, and the like means an interaction that typically is weaker than "binding," i.e., an interaction based upon hydrogen bonding, van der Waals binding, London forces, and/or other non-covalent interactions that contribute to an affinity of one molecule for another molecule, which affinity can be assisted by structural features such as the ability of one molecule to conform to another molecule or a section of another molecule. Molecule-molecule interactions can involve binding, but need not.

"Biomolecule," as used herein, means a molecule typically derived from a subject, and which typically includes building blocks including nucleotides, and the like. Examples include, but are not limited to, peptides, polypeptides, proteins, protein complexes, nucleotides, oligonucleotides, polynucleotides, nucleic acid complexes, saccharides, oligosaccharides, carbohydrates, lipids, etc., as well as combinations, enantiomers, homologs, analogs, derivatives and/or mimetics thereof.

"Species," as used herein, refers to a molecule or collection of molecules, for example, an inorganic chemical, an organic chemical, a biomolecule, or the like. In the present invention, species generally are biomolecules.

"Corresponding species," as used herein, means at least two different species that are identical chemically or, if they differ chemically and/or by molecular weight, differ only slightly. Examples of corresponding species include structural isoforms of proteins, proteins or other molecules that are essentially identical but that differ in binding affinity with respect to another species or plural species, have different higher-order structure, e.g., differing in secondary or tertiary structure but not differing or not differing significantly in chemical sequence. In general, corresponding species are species that may be arranged differently (isoforms, isomers, etc.) but are composed of the same or essentially the same chemical building blocks.

"Detectable," as used herein, refers the ability of a species and/or a property of the species to be discerned. One example method of rendering a species detectable is to provide further species that bind or interact with the first species, where the species comprise(s) a detectable label. Examples of detectable labels include, but are not limited to, nucleic acid labels, chemically reactive labels, fluorescence labels, enzymatic labels and radioactive labels.

"Mimetic," as used herein, includes a chemical compound, an organic molecule, or any other mimetic, the structure of which is based on, or derived from, a binding region of an antibody or antigen. For example, one can model predicted chemical structures to mimic the structure of a binding region, such as a binding loop of a peptide. Such modeling can be performed using standard methods (see, for example, Zhao et al., Nat. Struct. Biol. 2: 1131-1137 (1995)). The mimetics identified by methods such as this can be further characterized as having the same binding function as the originally identified molecule of interest, according to the binding assays described herein.

"Structure," "structural state," "configuration" or "conformation," as used herein, all refer to the commonly understood meanings of the respective terms, for example, as they apply to biomolecules such as proteins and nucleic acids, as well as pharmacologically active small molecules. In different contexts, the meaning of these terms will vary, as is appreciated by those of skill in the art. The structure or structural state of a molecule refers generally not to the building blocks that define the molecule but the spatial arrangement of these building blocks. The configuration or confirmation typically defines this arrangement. For instance, the use of the terms primary, secondary, tertiary or quaternary, in reference to protein structure, have accepted meanings within the art, which differ in some respects from their meaning when used in reference to nucleic acid structure (see, e.g., Cantor and Schimmel, Biophysical Chemistry, Parts I-III). Unless otherwise specified, the meanings of these terms will be those generally accepted by those of skill in the art.

"Physiological conditions," as used herein, means the physical, chemical, or biophysical state of a subject. As most typically used in the context of the present invention, physiological condition refers to a normal (e.g., healthy in the context of a human) or abnormal (e.g., in a diseased state in the context of a human) condition.

"Marker," as used herein, is a species that can be a carrier of information regarding a physiological state of a biological environment within which it resides. A marker can exhibit at least two different properties or values of a specific property or properties (e.g., structural conformation, binding affinity for another species, etc. but not solely different amounts of the species) that correspond to and/or that represent information regarding the two or more physiological states of environments within which they reside. For example, a marker may be a protein that is structurally modified between a first state representative of a healthy system within which it resides and a second structural state (different conformation) representative of a disease system within which it resides.

The term "cancer," as used herein, may include, but is not limited to: throat cancer, stomach cancer, pancreatic cancer, brain cancer, lung cancer, cervical cancer, prostate cancer, breast cancer, testicular cancer, ovarian cancer, oral cancer, throat cancer, esophagus cancer, and intestinal cancer and intestinal cancer.

The following documents are incorporated herein by reference: U.S. Pat. No. 7,968,350, issued Jun. 28, 2011, entitled "Characterization of Molecules," by Chait, et al.; U.S. Pat. No. 8,099,242, issued Jan. 17, 2012, entitled "Systems and Methods for Characterization of Molecules," by Chait, et al.; and International Patent Application No. PCT/US04/019343, filed Jun. 14, 2004, entitled "Systems and Methods for Characterization of Molecules," by Chait, et al., published as WO2004111655 on Dec. 23, 2004

The following examples are intended to illustrate certain embodiments of the present invention, but do not exemplify the full scope of the invention.

Example 1

This example shows that multiple proteins, which are being simultaneously assayed in a single aqueous two-phase partitioning system, may potentially serve as biomarkers by displaying differential partitioning behavior using blood plasma from subjects with prostate malignant tumor and subjects with benign prostate hyperplasia.

Human plasma samples corresponding to malignant and benign or healthy clinical phenotypes were purchased from SeraCare Life Sciences (Milford, MA). The diagnostic status of each sample was provided by SeraCare Life Sciences. Sample aliquots were thawed, brought to the room temperature, and combined in a pool composed of aliquots from subjects with the same disease status before introduction into an aqueous two-phase systems.

An aqueous two-phase system was prepared containing 15.7 wt % PEG-600 (molecular weight of about 600), 11.9 wt % Dextran-70 (molecular weight of about 70,000), 0.15 M NaCl, and 0.010 M sodium/potassium phosphate buffer, pH 7.4. The system in each tube was prepared by mixing the appropriate amounts of stock polymer and buffer solutions dispensed by a liquid handling workstation (Hamilton ML-4000) into a microtube having a total volume of 1.2 mL up to a total volume of a mixture of 393 microliters. 100 microliters of each plasma sample were added to a prepared system in a tube. The ratio between the volumes of the two phases of each system (having a final volume of 500 microliters) was 1:1. Each system was vigorously shaken and centrifuged for 60 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g, and used for further analysis.

A second aqueous two-phase system was prepared containing 15.7 wt % PEG-600 (polyethylene glycol with molecular weight of about 600), 11.9 wt % Dextran-70 (molecular weight of about 70,000), 0.15 M $Na_2SO_4$, and 0.010 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each plasma sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A third aqueous two-phase system was prepared containing 6.0 wt % PEG-8000 (polyethylene glycol with molecular weight of about 8,000), 12.2 wt % Dextran-70 (molecular weight of about 70,000), 2.3 M NaCl, and 0.010 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 375 microliters. 100 microliters of each plasma sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 40 microliters from the top and the bottom phases were withdrawn in duplicate. Each was diluted and mixed with appropriate reagents as indicated below and used for further analysis.

Immunoassay analysis of aliquots (each 200 microliters volume) from the top and the bottom phases was performed using the Bio-Plex suspension array system (Bio-Rad Laboratories, Hercules, CA). For each analyte, 100 beads were analyzed and mean values were calculated. The concentrations of analytes were quantified using a standard curve generated using Bio-Rad five-parameter curve-fitting to the series of known concentration of analytes. The partition coefficient for each analyte was calculated as the ratio of the analyte concentration determined in the top phase to that in the bottom phase.

The partition coefficients for several analytes examined in pools of plasma samples from subjects with the same diagnostic status of either prostate cancer or benign prostate condition are presented in Table 1 (partition coefficients for different proteins in plasma samples from subjects with diagnostic status indicated in different aqueous two-phase systems). The data presented in Table 1 demonstrate that a single aqueous partitioning system could be used to simultaneously study the partitioning behavior of multiple unique biomarkers. This example also illustrates that the solvent properties of the two aqueous phases in only a single system could nevertheless enable multiple protein biomarkers to be processed simultaneously, each exhibiting different degree of clinical separation between the disease/benign states.

TABLE 1

| Analyte* | Partition coefficient K for analyte in plasma from subjects | |
|---|---|---|
| | Benign prostate condition | Prostate cancer |
| PEG-600-Dex-70-NaCl—Na/K—PB | | |
| sVCAM-1 | 0.31 | 0.13 |
| NGF | 4.5 | 2.6 |
| Angiostatin | 5.9 | 2.4 |
| Thrombospondin | 0.48 | 0.052 |
| PAI-1 | 2.1 | 0.65 |
| Endostatin | 9.2 | 3.5 |
| MMP-2 | 3.5 | 0.97 |
| MMP-3 | 2.4 | 1.2 |
| PEG-600-Dex-70-Na$_2$SO$_4$—Na/K—PB | | |
| sVCAM-1 | 8.8 | 21.1 |
| sICAM-1 | 8.1 | 26 |
| MPO | 2.4 | 8.7 |
| tPAI-1 | 2.7 | 5.5 |
| MMP-9 | 6.8 | 85.3 |
| Kallikrein-10 | 0.96 | 1.63 |
| NGF | 16.96 | 30.8 |
| MMP-2 | 15.9 | 47.4 |
| Thrombospondin | 10.2 | 49.3 |
| PEG-8000-Dex-70-NaCl—Na/K—PB | | |
| MPO | 0.24 | 0.5 |
| tPAI-1 | 2.45 | 3.61 |
| MMP-9 | 4.1 | 6.5 |
| NGF | 5.7 | 2.95 |
| IGFBP-1 | 7.8 | 4.3 |
| Angiostatin | 9.9 | 2.7 |
| Thrombospondin | 1.1 | 0.32 |

*sVCAM-1—soluble vascular adhesion molecule; sICAM-1—soluble intercellular adhesion molecule; NGF—nerve growth factor; PAI-1—plasminogen activator inhibitor-1; MMP-2—matrix metallopeptidase 2; MMP-3—matrix metallopeptidase 3; MMP-9—matrix metallopeptidase 9; MPO—myeloperoxidase; tPAI-1—tissue plasminogen activator inhibitor-1; IGFBP-1—insulin-like growth factor-binding protein 1.

Example 2

This example shows that multiple proteins, which are being simultaneously assayed in a single aqueous two-phase partitioning system, could potentially serve as biomarkers by displaying different partitioning behavior using blood plasma from subjects with pancreatic malignant tumor and subjects with benign prostate hyperplasia.

Human plasma samples corresponding to malignant and benign or healthy clinical phenotypes were purchased from SeraCare Life Sciences. The diagnostic status of each sample was provided by SeraCare Life Sciences. Sample aliquots were thawed, brought to the room temperature, and combined in a pool composed of aliquots from 30 subjects with the same disease status before introducing into aqueous two-phase systems.

An aqueous two-phase system was prepared containing 15.7 wt % PEG-600 (molecular weight of about 600) and 18.1 wt % sodium/potassium phosphate buffer, pH 7.4. The system in each tube was prepared by mixing the appropriate amounts of stock polymer and buffer solutions dispensed by a liquid handling workstation (Hamilton ML-4000) into a microtube having a total volume of 1.2 mL up to a total volume of a mixture of 400 microliters. 100 microliters of each plasma sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A second aqueous two-phase system was prepared containing 15.7 wt % PEG-600 (polyethylene glycol with molecular weight of about 600), 9.5 wt % Na$_2$SO$_4$, 0.15 M NaCl, and 2.3 wt % sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each plasma sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A third aqueous two-phase system was prepared containing 18.0 wt % Ficoll®-70 (Ficoll® with molecular weight of about 70,000), 13.0 wt % Dextran-70 (molecular weight of about 70,000), 2.3 M NaCl, and 0.15 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each plasma sample was added to a prepared system in a tube. The ratio between the volumes of the two phases of each system (having a final volume of 500 microliters) was 1:1. Each system was vigorously shaken and centrifuged for 60 min at 3500 g in a refrigerated centrifuge with a microplate rotor with the temperature maintained at 23° C. to speed phase settling. The microtubes were taken out of the centrifuge, and aliquots of 40 microliters from the top and the bottom phases were withdrawn in duplicate. Each was diluted and mixed with appropriate reagents as indicated below and used for further analysis.

Immunoassay analysis of aliquots (each 200 microliters volume) from the top and the bottom phases was performed using the Bio-Plex suspension array system (Bio-Rad Laboratories, Hercules, CA). For each analyte, 100 beads were analyzed and mean values were calculated. The concentrations of analytes were quantified using a standard curve generated using Bio-Rad five-parameter curve-fitting to the series of known concentration of analytes. The partition coefficient for each analyte was calculated as the ratio of the analyte concentration determined in the top phase to that in the bottom phase.

The partition coefficients for several analytes examined in pools of plasma samples from subjects with the same diagnostic status of either pancreatic cancer or normal origin are presented in Table 2 (partition coefficients for different proteins in plasma samples from subjects with diagnostic status indicated in different aqueous two-phase systems). As discussed before, this example illustrates that the solvent properties of the two aqueous phases in only a single system could enable multiple protein biomarkers to be processed simultaneously, each exhibiting different degree of clinical separation between the disease and normal states.

TABLE 2

| Analyte* | Partition coefficient K for analyte in plasma from subjects | |
|---|---|---|
|  | Healthy donors | Pancreatic cancer |
| PEG-600-Na/K—PB | | |
| sVCAM-1 | 127 | 54 |
| MPO | 1.4 | 0.5 |
| MMP-9 | 132 | 61.6 |
| Thrombospondin | 3.53 | 7.13 |
| MMP-2 | 7 | 15.7 |
| PEG-600-Na$_2$SO$_4$—NaCl—Na/K—PB | | |
| sVCAM-1 | 2.36 | 32.3 |
| sICAM-1 | 21.5 | 71.2 |
| Kallikrein-10 | 1.11 | 1.94 |
| NGF | 9.2 | 34.1 |
| IGFBP-1 | 124 | 65 |
| Thrombospondin | 0.38 | 1.06 |
| MMP-2 | 36.4 | 23.6 |
| Ficoll-Dex-70-Na/K—PB | | |
| sICAM-1 | 14.8 | 9.1 |
| sVCAM-1 | 33.8 | 17.8 |
| Thrombospondin | 9.8 | 4.1 |
| MPO | 38.7 | 13 |
| MMP-9 | 30.1 | 19 |
| Angiostatin | 25.6 | 14.2 |
| Mesothelin | 3.8 | 2.0 |

*sVCAM-1—soluble vascular adhesion molecule; sICAM-1—soluble intercellular adhesion molecule; NGF—nerve growth factor; MMP-2—matrix metallopeptidase 2; MMP-9—matrix metallopeptidase 9; MPO—myeloperoxidase; IGFBP-1—insulin-like growth factor-binding protein 1.

Example 3

This example shows that multiple proteins, which are being simultaneously assayed in a single aqueous two-phase partitioning system, could potentially serve as biomarkers by displaying different partitioning behavior using blood serum from subjects with malignant breast tumors and subjects with benign breast tumors.

Human serum samples corresponding to malignant and benign or healthy clinical phenotypes were purchased from SeraCare Life Sciences. The diagnostic status of each sample was provided by SeraCare Life Sciences. Sample aliquots were thawed, brought to the room temperature, and combined in a pool composed of aliquots from 30 subjects with the same disease status before introducing into aqueous two-phase systems.

An aqueous two-phase system was prepared containing 15.7 wt % PEG-600 (polyethylene glycol with molecular weight of about 600), 9.5 wt % Na$_2$SO$_4$, 0.15 M NaCl, and 2.3 wt % sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A second aqueous two-phase system was prepared containing 15.7 wt % PEG-600 (polyethylene glycol with molecular weight of about 600), 9.5 wt % Na$_2$SO$_4$, 0.85 M NaCl, and 2.3 wt % sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A third aqueous two-phase system was prepared containing 15.7 wt % PEG-600 (polyethylene glycol with molecular weight of about 600), 0.15 M NaCl, and 18.1 wt % sodium/potassium phosphate buffer, pH 7.4. Each system was prepared by mixing the appropriate amounts of stock polymer, salt, and buffer solutions dispensed by a liquid handling workstation (Hamilton ML-4000) into a microtube of a total volume of 1.2 mL up to a total volume of a mixture of 375 microliters. 100 microliters of each serum sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling.

The microtubes were taken out of the centrifuge, and aliquots of 40 microliters from the top and the bottom phases were withdrawn in duplicate. Each was diluted and mixed with appropriate reagents as indicated below and used for further analysis.

Immunoassay analysis of aliquots (each 200 microliters volume) from the top and the bottom phases was performed using the Bio-Plex suspension array system (Bio-Rad Laboratories, Hercules, CA). For each analyte, 100 beads were analyzed and means were calculated. The concentrations of analytes were quantified using a standard curve generated using Bio-Rad five-parameter curve-fitting to the series of known concentration of analytes. The partition coefficient for each analyte was calculated as the ratio of the analyte concentration determined in the top phase to that in the bottom phase.

The partition coefficients for several analytes examined in pools of serum samples from subjects with the same diagnostic status of either breast cancer or benign are presented in Table 3 (partition coefficients for different proteins in serum samples from subjects with diagnostic status indicated in different aqueous two-phase systems). The data presented in Table 3 demonstrate that there is a difference between partition behavior of indicated proteins in serum from subjects with malignant breast tumor and from subjects with benign breast tumor, and that this difference was displayed to a different degree in different aqueous two-phase systems. One will note that the change in K values is not unidirectional: from benign to malignant states, some K values increase, while others show a decrease.

TABLE 3

| Analyte* | Partition coefficient K for analyte in serum from subjects | |
|---|---|---|
| | Benign breast tumor | Breast cancer |
| PEG-600-Na$_2$SO$_4$-0.15M NaCl—Na/K—PB | | |
| sVCAM-1 | 1.63 | 0.72 |
| sICAM-1 | 18.8 | 9.8 |
| tPAI-1 | 35.4 | 17.8 |
| MMP-9 | 43.2 | 22.8 |
| Angiostatin | 51 | 24.6 |
| MMP-2 | 9.65 | 3.59 |
| PEG-600-Na$_2$SO$_4$-0.85M NaCl—Na/K—PB | | |
| sVCAM-1 | 2.35 | 0.94 |
| sICAM-1 | 19.7 | 10.2 |
| MPO | 3.2 | 0.86 |
| Thrombospondin | 123 | 39.4 |
| PAI-1 | 3.12 | 1.19 |
| MMP-2 | 28.2 | 8.8 |
| PEG-600-NaCl—Na/K—PB | | |
| sICAM-1 | 8.12 | 12.64 |
| tPAI-1 | 18.96 | 34.4 |
| MMP-9 | 15.8 | 41.4 |
| Angiostatin | 33 | 62 |
| Thrombospondin | 0.20 | 0.66 |
| PAI-1 | 0.77 | 1.86 |
| MMP-2 | 10.4 | 26.7 |

*sVCAM-1—soluble vascular adhesion molecule; sICAM-1—soluble intercellular adhesion molecule; NGF—nerve growth factor; PAI-1—plasminogen activator inhibitor-1; MMP-2—matrix metallopeptidase 2; MMP-9—matrix metallopeptidase 9; MPO—myeloperoxidase; tPAI-1—tissue plasminogen activator inhibitor-1; PAI-1—plasminogen activator inhibitor-1.

Example 4

This examples shows that different proteins could potentially serve as biomarkers displaying different partition behavior upon assay in a single aqueous two-phase system, when present in blood serum from subjects with malignant ovarian tumor and healthy donors.

Human serum samples corresponding to malignant and benign or healthy clinical phenotypes were purchased from SeraCare Life Sciences. The diagnostic status of each sample was provided by SeraCare Life Sciences. Sample aliquots were thawed, brought to the room temperature, and combined in a pool composed of aliquots from 30 subjects with the same disease status before introducing into aqueous two-phase systems.

An aqueous two-phase system was prepared containing 15.7 wt % PEG-600 (polyethylene glycol with molecular weight of about 600), 11.9 wt % Dextran-70 (dextran with molecular weight of about 70,000), 0.15 M NaCl, and 0.01 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a prepared system in a tube. The ratio between the volumes of the two phases of each system (having a final volume of 500 microliters) was 1:1. Each system was vigorously shaken and centrifuged for 30 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A second aqueous two-phase system was prepared containing 18.0 wt % Ficoll®-70 (Ficoll® with molecular weight of about 70,000), 13.0 wt % Dextran-70 (dextran with molecular weight of about 70,000), and 0.15 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a prepared system in a tube. The ratio between the volumes of the two phases of each system (having a final volume of 500 microliters) was 1:1. Each system was vigorously shaken and centrifuged for 60 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

A third aqueous two-phase system was prepared containing 18.0 wt % Ficoll®-70 (Ficoll® with molecular weight of about 70,000), 13.0 wt % Dextran-70 (dextran with molecular weight of about 70,000), 0.15 M Na$_2$SO$_4$, and 0.01 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a prepared system in a tube. The ratio between the volumes of the two phases of each system (having a final volume of 500 microliters) was 1:1. Each system was vigorously shaken and centrifuged for 60 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

Immunoassay analysis of aliquots (each 200 microliters volume) from the top and the bottom phases was performed using the Bio-Plex suspension array system (Bio-Rad Laboratories, Hercules, CA). For each analyte, 100 beads were analyzed and means were calculated. The concentrations of analytes were quantified using a standard curve generated using Bio-Rad five-parameter curve-fitting to the series of known concentration of analytes. The partition coefficient for each analyte was calculated as the ratio of the analyte concentration determined in the top phase to that in the bottom phase.

The partition coefficients for several analytes examined in pools of serum samples from subjects with the same diagnostic status of either ovarian cancer or normal are presented in Table 4 (partition coefficients for different proteins in serum samples from subjects with diagnostic status indicated in different aqueous two-phase systems). It is evident that the conclusions regarding the applicability of a single aqueous two-phase system to analyze multiple protein biomarkers hold also in the case of ovarian cancer.

TABLE 4

| Analyte* | Partition coefficient K for analyte in serum from subjects | |
|---|---|---|
| | Healthy donors | Ovarian cancer |
| PEG-600-Dex-NaCl—Na/K—PB | | |
| sE-Selectin | 0.36 | 0.74 |
| sVCAM-1 | 0.09 | 0.20 |
| Thrombospondin | 11.44 | 28.7 |
| MMP-9 | 43.2 | 22.8 |
| AFP | 1.09 | 0.57 |
| Ficoll-Dex-Na/K—PB | | |
| sVCAM-1 | 8.9 | 16.4 |
| sICAM-1 | 6.4 | 8.3 |
| MMP-9 | 9.2 | 12 |
| IGFBP-1 | 2.97 | 5.14 |
| Angiostatin | 5.74 | 23 |
| Mesothelin | 1.48 | 4.27 |
| Prolactin | 10.4 | 13.9 |
| Ficoll-Dex-Na$_2$SO$_4$—Na/K—PB | | |
| sE-Selectin | 2.3 | 4.2 |
| Angiostatin | 10.3 | 15.6 |
| Thrombospondin | 5.8 | 14.1 |
| Mesothelin | 2.56 | 4.18 |

*sVCAM-1—soluble vascular adhesion molecule; sICAM-1—soluble intercellular adhesion molecule; MMP-9—matrix metallopeptidase 9; IGFBP-1—insulin-like growth factor-binding protein 1; AFP—alpha fetoprotein.

Example 5

This example illustrates using ovarian cancer and healthy samples to derive diagnostically useful information from simultaneously partitioning multiple biomarkers in biological fluids using a single partitioning system. It is demonstrated that the differential partitioning of biomarkers between the two aqueous phases based on their correspondence to a disease state could be studied by measuring the concentration of a biomarker in a single phase, instead of measuring the concentration in both phases and calculating the partition coefficient, K.

Human serum samples corresponding to malignant and benign or healthy clinical phenotypes were purchased from SeraCare Life Sciences. The diagnostic status of each sample was provided by SeraCare Life Sciences. Sample aliquots were thawed, brought to the room temperature, and combined in a pool composed of aliquots from 30 subjects with the same disease status before introducing into aqueous two-phase systems.

An aqueous two-phase system was prepared containing 18.0 wt % Ficoll®-70 (Ficoll® with molecular weight of about 70,000), 13.0 wt % Dextran-70 (dextran with molecular weight of about 70,000), and 0.15 M sodium/potassium phosphate buffer, pH 7.4. The system in each tube was prepared by mixing the appropriate amounts of stock polymer, salt, and buffer solutions dispensed by a liquid handling workstation (Hamilton ML-4000) into a microtube having a total volume of 1.2 mL up to a total volume of a mixture of 400 microliters. 100 microliters of each serum sample was added to a system. The ratio between the volumes of the two phases of each system (having a final volume of 500 microliters) was 1:1. Each system was vigorously shaken and centrifuged for 60 min at 3500 g in a refrigerated centrifuge with a microplate rotor with the temperature maintained at 23° C. to speed phase settling. The microtubes were taken out of the centrifuge, and aliquots of 50 microliters from the top and the bottom phases were withdrawn in duplicate. Each was diluted 5-fold, mixed, centrifuged for 5 min at 3000 g and used for further analysis.

Immunoassay analysis of aliquots (each 200 microliters volume) from the top and the bottom phases was performed using the Bio-Plex suspension array system (Bio-Rad Laboratories, Hercules, CA). For each analyte, 100 beads were analyzed and means were calculated. The concentrations of analytes were quantified using standard curve generated using Bio-Rad five-parameter curve-fitting to the series of known concentration of analytes.

Figure 4:
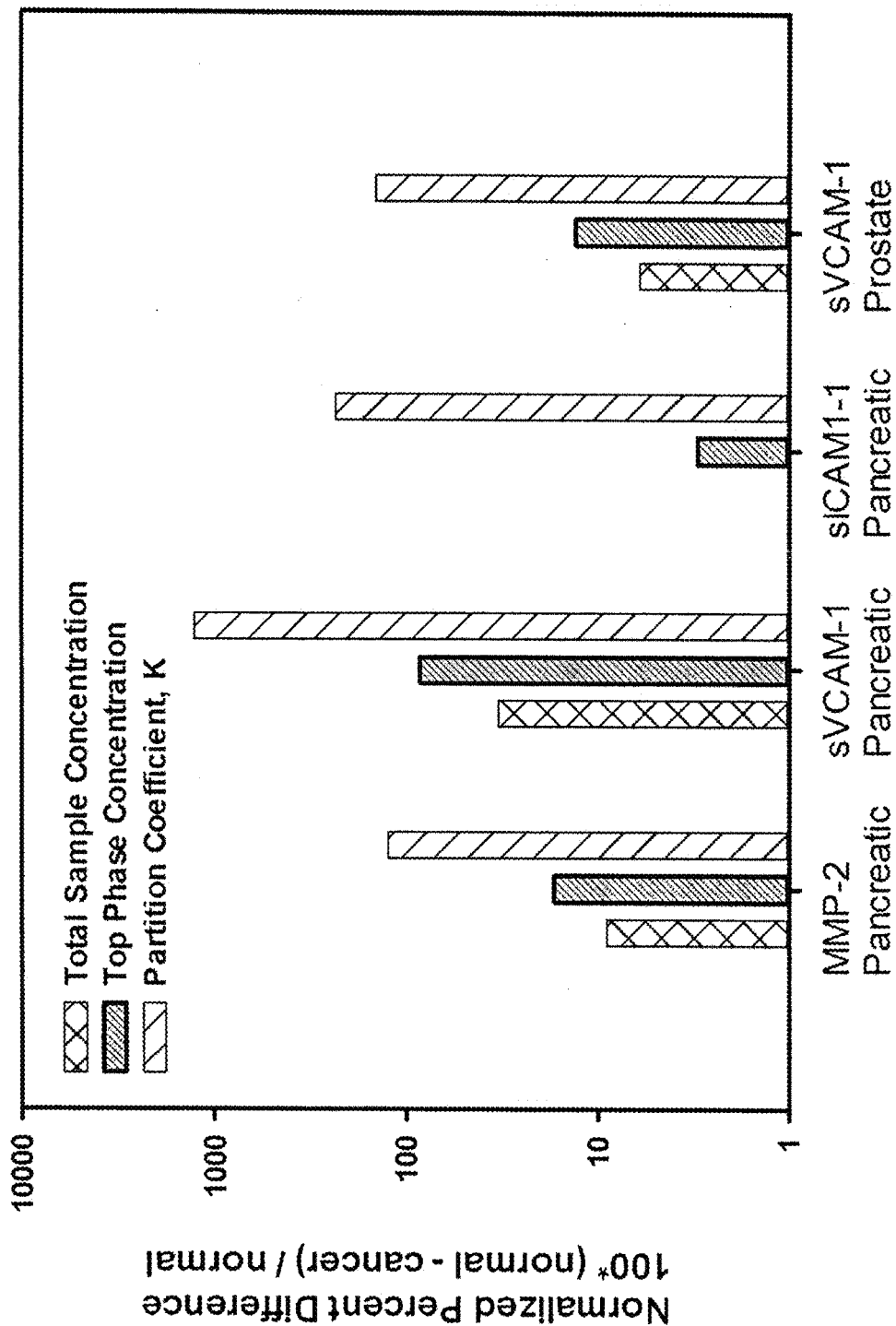
FIG. 4 shows the normalized differences between normal and cancer samples using three different determination methods, including conventional sample concentration measurement, and various embodiments of the present invention as applied to the same samples: measurement of concentration in the top phase alone of an aqueous partitioning system, and determination of the partition coefficient (K) of the same partitioning system.

The concentrations for several analytes in top aqueous phase were measured followed partitioning of pools of serum samples from subjects with same diagnostic status of cancer or benign/normal are presented in Table 5 (concentrations for different proteins in top phase of aqueous two-phase system for pools of serum from subjects with indicated diagnostic status). The concentration values for the top phase and total raw sample concentrations are noted. The K values for the particular proteins/cancer/SIA combinations corresponded to the values provided in Tables 1 and 2. The normalized difference (delta) between the benign/normal and cancer cases is calculated for each of the three assay options, using the top phase concentration data alone, the total sample concentration alone, or the K value. FIG. 4 illustrates the normalized difference data in Table 5.

It is evident that for the same biomarker/cancer type/SIA composition, the largest difference between the two states was always found between the K values. If only a single concentration measurement is desired for simplicity and cost considerations (K requires at least two concentration measurements for calculation), then the data demonstrate that it may be advantageous to measure the concentration of a single phase following partitioning, instead of the incoming sample concentration. Given the natural variability in both normal/benign and cancer populations, it may be difficult or impossible to determine a diagnosis of cancer, as an example, unless the concentration level of the sample is significantly different from that corresponding to normal/benign conditions. Thus, partitioning the sample in SIA with particular composition such that, e.g., the biomarker protein will preferentially segregate to the top phase in cancer over that corresponding to normal/benign, may result in better and more significant differentiation between samples based on their disease state. While K differentiation may be more significant, the simplicity and cost advantages of conducting a single measurement of the analyte concentration could sometime be positively exploited if done following sample partitioning.

numbers and all the fractional and integral numerals therebetween. As used herein the term "about" refers to +/−10%.

While several embodiments of the present invention have been described and illustrated herein, those of ordinary skill in the art will readily envision a variety of other means and/or structures for performing the functions and/or obtaining the results and/or one or more of the advantages

TABLE 5

| SIA # | Cancer | Protein | Top phase conc ben/nor | Top phase conc cancer | Total conc ben/nor | Total conc cancer | K ben/nor | K cancer | Delta top phase conc | Delta K | Delta total conc |
|---|---|---|---|---|---|---|---|---|---|---|---|
| 1 | Pancreatic | MMP-2 | 15284 | 17951 | 8734 | 9547 | 7 | 15.7 | 17% | 124% | 9% |
| 2 | Pancreatic | sVCAM-1 | 27013 | 49710 | 19230 | 25625 | 2.36 | 32.3 | 84% | 1269% | 33% |
| 2 | Pancreatic | sICAM-1 | 10065 | 10345 | 5267 | 5245 | 21.5 | 71.2 | 3% | 231% | 0% |
| 3 | Prostate | sVCAM-1 | 34866 | 39341 | 19414 | 20598 | 8.8 | 21.1 | 13% | 141% | 6% |

SIA #1: PEG-600-Na/K-PB;
SIA #2: PEG-600-Na$_2$SO$_4$—NaCl—Na/K-PB;
SIA #3: PEG-600-Dex-70-Na$_2$SO$_4$—Na/K-PB
Concentrations are in pg/ml.
Delta is defined in percent as: (benign/normal value − cancer value)/benign/normal value.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. The present invention could be employed for general population screening and one could use change the biomolecules used or add additional biomolecules if by doing so, one would add to the accuracy of the diagnosis.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Any relevant liquid-based partitioning system may be appropriate for the instant invention, beyond those specifically described in the examples above. Higher level partitioning systems involving three or more solvents may be employed, though not directly described herewith.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for determining a risk level of cancer in a subject having an unknown type of cancer, the method comprising:
   providing a biological fluid sample taken from the subject, wherein the sample comprises at least a first biomolecular species and a second biomolecular species;
   partitioning the sample in an aqueous multi-phase system, wherein the first biomolecular species and the second biomolecular species partition differently in the aqueous multi-phase system, and the first biomolecular species and the second biomolecular species are each soluble in at least one phase of the aqueous multi-phase system;
   determining partition coefficients for the first biomolecular species and the second biomolecular species in at least a first phase and a second phase of the aqueous multi-phase system, using at least a first assay specific to the first biomolecular species to determine the first biomolecular species and a second assay specific to the second biomolecular species to determine the second biomolecular species, wherein the second phase is substantially immiscible with the first phase at equilibrium;
   comparing the partition coefficients of the first biomolecular species and the second biomolecular species with reference values to determine the presence or risk level of said unknown type of cancer in said subject based on a significant difference between the partition coefficients and the reference values, wherein the reference values are from individuals with and without cancer;
   determining a type of cancer within the subject having the unknown type of cancer based on the comparing step;
   selecting an anti-cancer drug or an anti-cancer therapeutic intervention for the subject based on the partition coefficients; and
   treating the subject for said cancer with the anti-cancer drug or the anti-cancer therapeutic intervention.

2. The method of claim 1, wherein the reference values are reference partition coefficients.

3. The method of claim 1, wherein the aqueous partitioning system comprises polyethylene glycol.

4. The method of claim 1, wherein the aqueous partitioning system comprises dextran.

5. The method of claim 1, wherein the cancer is prostate cancer.

6. The method of claim 1, wherein the cancer is pancreatic cancer.

7. The method of claim 1, wherein the cancer is breast cancer.

8. The method of claim 1, wherein the cancer is ovarian cancer.

9. The method of claim 1, wherein the aqueous multi-phase system is a two-phase system.

10. The method of claim 1, wherein the aqueous multi-phase system comprises at least three phases.

11. The method of claim 1, wherein at least one of the first assay or the second assay is a species-specific immuno-based assay.

12. The method of claim 1, wherein at least one of the first assay or the second assay is an ELISA (enzyme-linked immunosorbent assay).

13. The method of claim 1, wherein said reference values comprise known concentration values in corresponding aqueous phases derived from biological fluid samples taken from the individuals with and without cancer.

14. The method of claim 1, wherein the sample is selected from the group consisting of whole blood, blood serum, blood plasma, saliva, urine, CNS (central nervous system) fluid, breast nipple aspirate fluid, cerebral spinal fluid, and semen.

15. A method for determining a risk level of cancer in a subject having an unknown type of cancer, the method comprising:

providing a biological fluid sample taken from the subject, wherein the sample comprises at least a first biomolecular species and a second biomolecular species;

partitioning the sample in an aqueous multi-phase system, wherein the first biomolecular species and the second biomolecular species partition differently in the aqueous multi-phase system, and the first biomolecular species and the second biomolecular species are each soluble in at least one phase of the aqueous multi-phase system;

determining partitioning of the first biomolecular species and the second biomolecular species within the aqueous multi-phase system using at least a first assay specific to the first biomolecular species to determine the first biomolecular species and a second assay specific to the second biomolecular species to determine the second biomolecular species;

comparing the differences in partitioning of the first biomolecular species and the second biomolecular species with reference values to determine the presence or risk level of said unknown type of cancer in said subject based on a significant difference between the differences in partitioning and the reference values, wherein the reference values are from individuals with and without cancer;

determining a type of cancer within the subject having an unknown type of cancer based on the difference in partitioning of the first biomolecular species and the second biomolecular species;

selecting an anti-cancer drug or an anti-cancer therapeutic intervention for the subject based on the partition coefficients; and treating the subject for said cancer with the anti-cancer drug or the anti-cancer therapeutic intervention.

16. The method of claim 15, wherein the cancer is prostate cancer.

17. The method of claim 15, wherein the cancer is pancreatic cancer.

18. The method of claim 15, wherein the cancer is breast cancer.

19. The method of claim 15, wherein the cancer is ovarian cancer.

20. The method of claim 15, wherein the aqueous multi-phase system is a two-phase system.

21. The method of claim 15, wherein at least one of the first assay or the second assay is a species-specific immuno-based assay.

22. The method of claim 15, wherein at least one of the first assay or the second assay is an ELISA (enzyme-linked immunosorbent assay).

23. The method of claim 15, wherein the sample is selected from the group consisting of whole blood, blood serum, blood plasma, saliva, urine, CNS (central nervous system) fluid, breast nipple aspirate fluid, cerebral spinal fluid, and semen.

* * * * *